US012318299B2

(12) United States Patent
Quintana-Ponce et al.

(10) Patent No.: US 12,318,299 B2
(45) Date of Patent: Jun. 3, 2025

(54) COATED IMPLANT AND METHOD OF MAKING THE SAME

(71) Applicant: DePuy Synthes Products, Inc., Raynham, MA (US)

(72) Inventors: Oscar A. Quintana-Ponce, Goshen, IN (US); Bryan J. Smith, Fort Wayne, IN (US); Craig N. Ernsberger, Granger, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 576 days.

(21) Appl. No.: 17/179,827

(22) Filed: Feb. 19, 2021

(65) Prior Publication Data

US 2021/0251766 A1 Aug. 19, 2021

Related U.S. Application Data

(60) Provisional application No. 63/010,300, filed on Apr. 15, 2020, provisional application No. 62/978,534, filed on Feb. 19, 2020, provisional application No. 62/978,537, filed on Feb. 19, 2020.

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2002/30011* (2013.01); *A61F 2002/3863* (2013.01); *A61F 2310/00023* (2013.01); *A61F 2310/00089* (2013.01); *A61F 2310/00095* (2013.01); *A61F 2310/00131* (2013.01); *A61F 2310/00149* (2013.01); *A61F 2310/00892* (2013.01)

(58) Field of Classification Search
CPC .......... A61F 2/28; A61F 2/3859; A61F 2/389; A61F 2/3868
See application file for complete search history.

(56) References Cited

U.S. PATENT DOCUMENTS

| 3,643,658 | A | 2/1972 | Steinemenan |
| 5,037,438 | A | 8/1991 | Davidson |
| 5,169,597 | A | 12/1992 | Davidson et al. |
| 5,370,694 | A | 12/1994 | Davidson |
| 5,980,974 | A | 11/1999 | Armini et al. |
| 7,157,096 | B2 | 1/2007 | Zhang et al. |

(Continued)

FOREIGN PATENT DOCUMENTS

| CN | 101596607 A | 12/2009 |
| CN | 102181835 A | 9/2011 |

(Continued)

OTHER PUBLICATIONS

Cui, Wenfang et al., "Bio-tribocorrosion behavior of nanocrystalline TiZrN coating on biomedical titanium alloy," Surface & Coatings Technology 369 (2019) 79-86.

(Continued)

*Primary Examiner* — Bruce E Snow
(74) *Attorney, Agent, or Firm* — Barnes & Thornburg LLP

(57) ABSTRACT

An orthopaedic knee implant includes a femoral component having a substrate and a coating disposed on the surface of (Continued)

the substrate. A method for making a femoral component of an orthopaedic knee implant is also disclosed.

23 Claims, 17 Drawing Sheets

(56) References Cited

U.S. PATENT DOCUMENTS

| | | | |
|---|---|---|---|
| 7,393,589 | B2 | 7/2008 | Aharonov |
| 7,790,216 | B2 | 9/2010 | Popoola et al. |
| 8,147,560 | B2 * | 4/2012 | Zeller .................... C23C 28/36 623/23.56 |
| 8,187,620 | B2 | 5/2012 | Chandrasekaran et al. |
| 8,790,345 | B2 | 7/2014 | Anderson |
| 9,005,769 | B2 | 4/2015 | Lambert |
| 9,404,173 | B2 | 8/2016 | Walker |
| 10,272,177 | B2 | 4/2019 | Khowaylo |
| 10,543,297 | B2 | 1/2020 | Pawar |
| 2004/0002766 | A1 * | 1/2004 | Hunter ................. A61L 27/306 623/22.17 |
| 2004/0122524 | A1 | 6/2004 | Hunter et al. |
| 2008/0255674 | A1 * | 10/2008 | Rahaman ............. C23C 28/042 623/23.11 |
| 2009/0054985 | A1 | 2/2009 | Anderson |
| 2009/0125115 | A1 * | 5/2009 | Popoola .................... A61F 2/38 623/20.14 |
| 2009/0187255 | A1 | 7/2009 | Jani et al. |
| 2011/0066253 | A1 | 3/2011 | Langhorn et al. |
| 2011/0112651 | A1 * | 5/2011 | Blaylock ............. A61F 2/30734 623/20.15 |
| 2012/0035739 | A1 | 2/2012 | Wilhemsson et al. |
| 2013/0216420 | A1 | 8/2013 | Li et al. |
| 2013/0230640 | A1 * | 9/2013 | Pawar ....................... C23C 8/34 427/2.27 |

FOREIGN PATENT DOCUMENTS

| | | |
|---|---|---|
| CN | 102277554 A | 12/2011 |
| JP | 2006511272 A | 4/2006 |
| JP | 2012110704 A | 6/2012 |

OTHER PUBLICATIONS

Donohue, L.A. et al., "Deposition and characterization of arc-bond sputter $Ti_xZr_yN$ coatings from pure metallic and segmented targets," Surface and Coatings Technology 75 (1995) 128-138.

Huang, Jia-Hong et al., "Evaluation of the fracture toughness of $Ti_{1-x}Zr_xN$ hard coatings: Effect of compositions," Surface & Coatings Technology 358 (2019) 487-496.

Huang, Jia-Hong et al., "Oxidation behavior and corrosion resistance of vacuum annealed ZrN-coated stainless steel," Surface & Coatings Technology 358 (2019) 308-319.

Huang, Jia-Hong et al., "Phase transition and mechanical properties of $ZrN_xO_y$ thin films of AISI 304 stainless steel," Surface & Coatings Technology 206 (2011) 107-116.

Lin, Yu-Wei et al., "Effect of Ti interlayer thickness on mechanical properties and wear resistance of TiZrN coatings on AISI D2 steel," Surface & Coatings Technology 394 (2020) 125690.

Milošev, I. et al., "Comparison of TiN, ZrN and CrN hard nitride coatings: Electrochemical and thermal oxidation," Thin Solid Films 303 (1997) 246-254.

Qi, Z.B. et al., "In situ and ex situ studies of microstructure evolution during high-temperature oxidation of ZrN hard coating," Scripta Materialia 97 (2015) 9-12.

Patent Cooperation Treaty Invitation to Pay Fees for corresponding International Application No. PCT/IB2021/051430, dated May 12, 2021, 14 pages.

Advanced Surface Technology Why Take a Chance With Anything Else, Aesculap Implant Systems, 2017, 12 pages.

\* cited by examiner

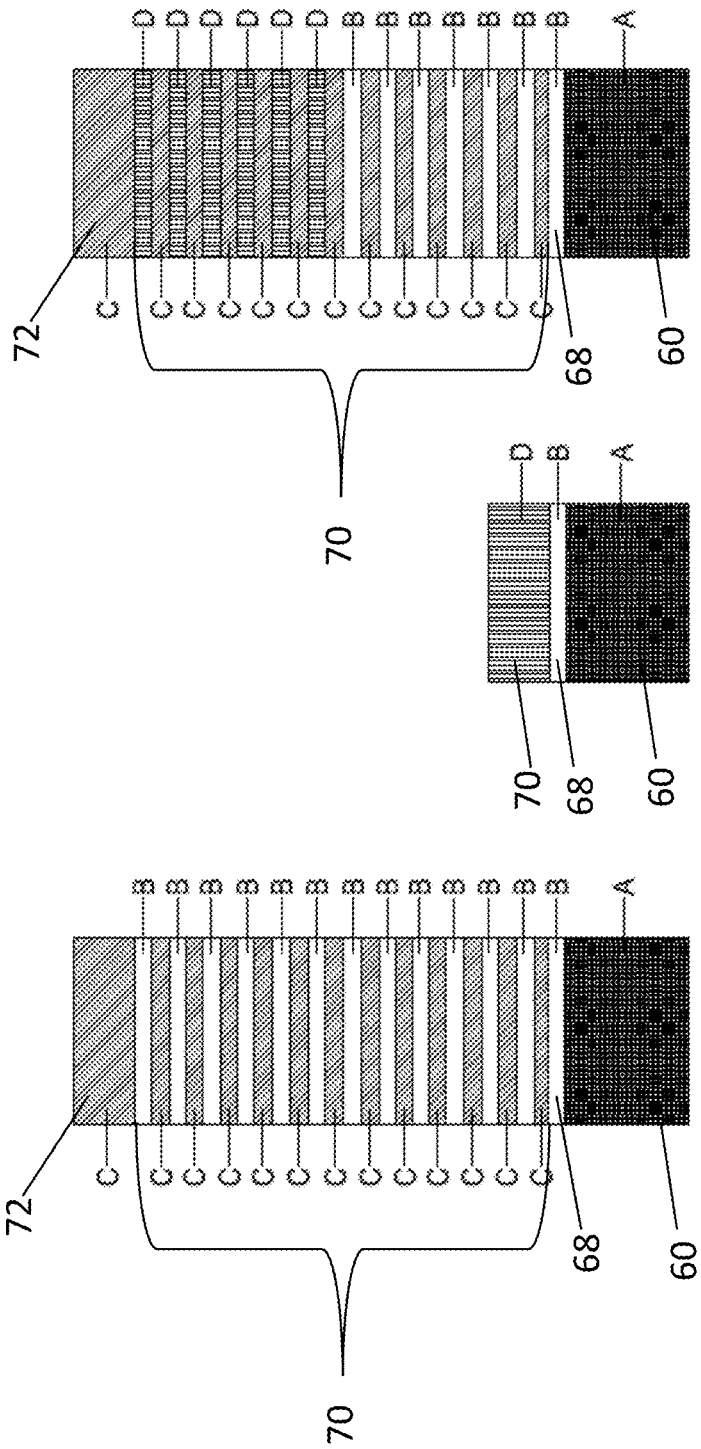

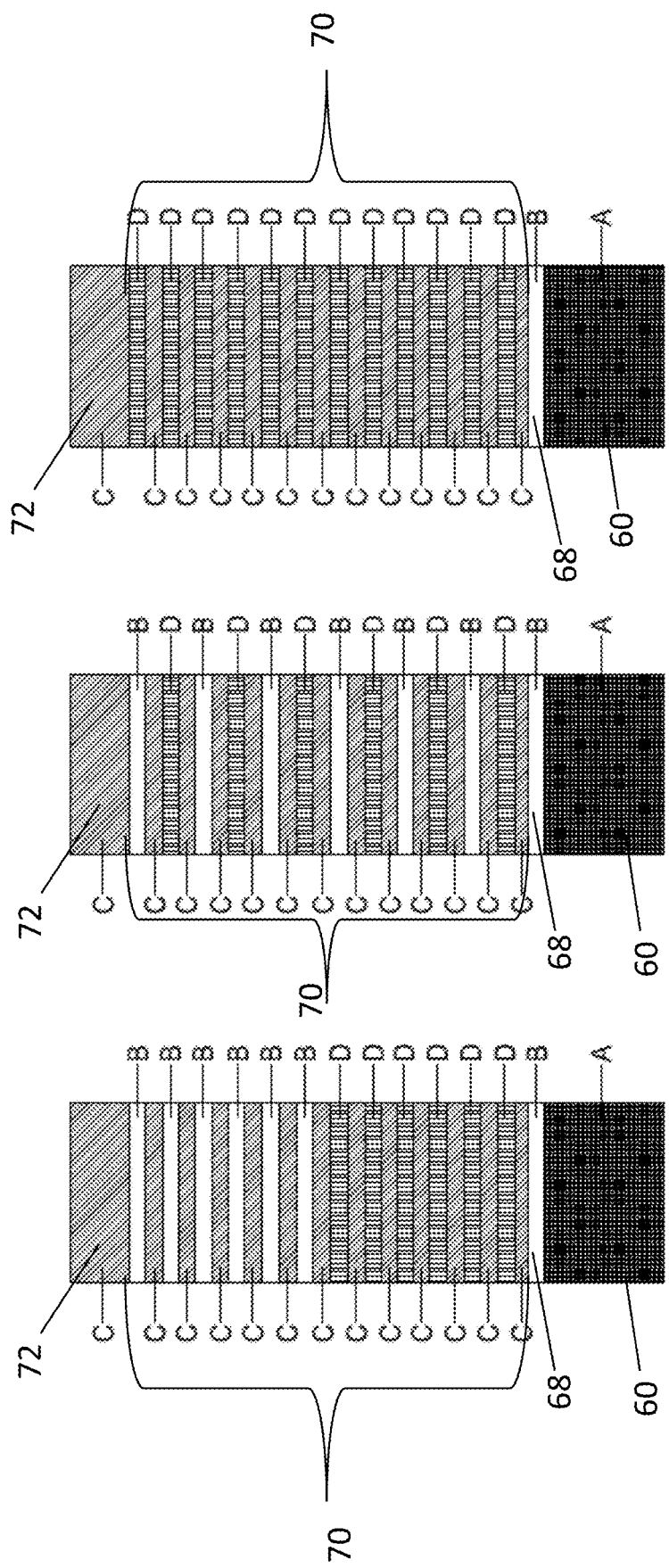

COATED IMPLANT AND METHOD OF MAKING THE SAME

This application claims priority to U.S. Provisional Application 62/978,534, filed Feb. 19, 2020, U.S. Provisional Application 62/978,537, filed Feb. 19, 2020, and U.S. Provisional Application 63/010,300, filed Apr. 15, 2020, the contents of each is incorporated herein by reference.

CROSS REFERENCE TO RELATED APPLICATIONS

Cross reference is made to pending International Application Serial No. PCT/IB2021/051431 titled "COATED IMPLANT AND METHOD OF MAKING THE SAME" and International Application Serial No. PCT/IB2021/051430 titled "COATED IMPLANT AND METHOD OF MAKING THE SAME," each of which is hereby incorporated by reference.

TECHNICAL FIELD

The present disclosure relates generally to an implantable orthopaedic prosthesis, and more particularly to a femoral component of an implantable orthopaedic prosthesis.

BACKGROUND

Joint arthroplasty is a well-known surgical procedure by which a diseased and/or damaged natural joint is replaced by a prosthetic joint. A typical knee prosthesis includes a patella prosthetic component, a tibial tray, a femoral component, and a tibial bearing positioned between the tibial tray and the femoral component. Femoral components are designed to be attached to a surgically-prepared distal end of a patient's femur. Tibial trays are designed to be attached to a surgically-prepared proximal end of a patient's tibia.

The femoral component and the tibial tray can be made of biocompatible materials such as metal alloys of cobalt-chrome. The tibial bearing component disposed between the femoral component and the tibial tray can be formed from a plastic material like polyethylene. However, cobalt alloys tend to be expensive, and accordingly, a need exists for a component made from a non-cobalt metal material and a method of manufacturing the same. For example, a need exists for a femoral component of a knee prosthesis out of a non-cobalt metal material and a method for manufacturing the same.

SUMMARY

According to an aspect of the disclosure, an orthopaedic implant includes a femoral component. The femoral component may be configured to be coupled to the distal end of a patient's femur. The femoral component includes a substrate that comprises a titanium alloy. Illustratively, the substrate has a condylar surface that is curved in a sagittal plane and a bone-facing surface positioned opposite the condylar surface. An articular layer (also referred to as a "coating") is disposed on the condylar surface. The coating comprises a first layer (also referred to as a "bonding layer" or "inner layer") comprising niobium, zirconium, titanium, tantalum, platinum, molybdenum, or combinations thereof. The coating also comprises a second layer (also referred to as an "intermediate layer") comprising a number of alternating sublayers. The coating further comprises a third layer (also referred to as an "outer layer") comprising zirconium oxide, niobium oxide, zirconium oxynitride, niobium oxynitride, titanium, or a combination thereof. The first layer extends between and interconnects the second layer and the condylar surface. The second layer extends between and interconnects the first layer and the third layer. The third layer forms an outer articular surface of the femoral component.

In some embodiments, the second layer may comprise at least eight sublayers of alternating zirconium nitride and niobium nitride sublayers. In some embodiments, each zirconium nitride sublayer of the alternating sublayers may have a thickness of about 0.5 nm to about 200 nm. In some embodiments, the second layer may have a thickness of about 3 μm to about 6 μm.

In some embodiments, the third layer may comprise at least about 90% monoclinic oxidized zirconium. In some embodiments, the third layer may have a thickness of about 100 nm to about 5 μm.

In some embodiments, at least one sublayer of the second layer may comprise at least about 95% zirconium nitride.

In some embodiments, at least one sublayer of the second layer may have a thickness of about 5 nm to about 500 nm. In some embodiments, at least one sublayer of the second layer may comprise at least about 95% niobium nitride.

In some embodiments, the first layer may comprise at least about 90% zirconium. In some embodiments, the first layer may have a thickness of about 50 nm to about 1 μm.

Illustratively, the femoral component may include a bone-engaging layer disposed on the bone-facing surface. In some embodiments, the bone-engaging layer may be porous.

In some embodiments, the second layer may comprise an inner sublayer and an outer sublayer. In some embodiments, the inner sublayer and the outer sublayer may have the same composition. In some embodiments, the second layer may comprise an intermediate sublayer having a composition different from the inner sublayer, the outer sublayer, or both.

In some embodiments, the third layer may be titanium zirconium nitride. Additionally, in some embodiments, the atomic percent of zirconium in the third layer may be 50 At % to 80 At %. In some embodiments, the atomic percent of zirconium in the third layer may be 30 At % to 85 At %.

In some embodiments, the number of alternating sublayers include a number of titanium zirconium nitride sublayers and a number of metallic layers. In some embodiments, the atomic percent of zirconium in the plurality of alternating sublayers is 30 At % to 85 At %. Additionally, in some embodiments, the atomic percent of zirconium-titanium alloy in the plurality of alternating sublayers is 30 At % to 85 At %.

According to another aspect, a process for forming a femoral component of an orthopaedic knee implant includes depositing a first layer comprising niobium, zirconium, titanium, tantalum, platinum, molybdenum, or combinations thereof, on a condylar surface of a substrate. The substrate comprises titanium. The condylar surface is curved in a sagittal plane. In some embodiments, the process includes depositing a second layer that comprises a number of alternating sublayers.

In some embodiments, the process may include oxidizing a portion of the second layer to form a third layer comprising oxidized zirconium.

In some embodiments, the alternating sublayers may comprise a sublayer of zirconium nitride and a sublayer of niobium. In some embodiments, depositing the number of alternating sublayers to form the second layer may comprise (a) creating a sublayer of zirconium nitride on the first layer, (b) creating a sublayer of niobium on the sublayer of zirconium nitride, and (c) repeating steps (a) and (b) to form the second layer.

In some embodiments, the process may include depositing a third layer on an outer surface of the second layer. In some embodiments, the third layer may comprise zirconium oxide, niobium oxide, zirconium oxynitride, niobium oxynitride, or a combination thereof.

Additional Embodiments are also contemplated.

Clause 1. An orthopaedic knee implant comprising: a femoral component configured to be coupled to a distal end of a patient's femur, the femoral component comprising (i) a substrate comprising a titanium alloy having (a) a condylar surface that is curved in a sagittal plane and (b) a bone-facing surface positioned opposite the condylar surface; and (ii) a coating disposed on the condylar surface, the coating comprising (a) a first layer comprising niobium, zirconium, titanium, tantalum, platinum, molybdenum, or combinations thereof, (b) a second layer comprising a number of alternating sublayers, and (c) a third layer comprising (i) a tetragonal zirconium oxide layer and (ii) a monoclinic zirconium oxide layer, wherein (i) the first layer extends between and interconnects the second layer and the condylar surface, (ii) the second layer extends between and interconnects the first layer and the third layer, and (iii) the third layer forms an outer surface of the coating.

Clause 2. The orthopaedic knee implant of clause 1, wherein the second layer further comprises a sublayer comprising zirconium.

Clause 3. The orthopaedic knee implant of clause 2, wherein each of the zirconium sublayers comprises at least about 70% tetragonal zirconium.

Clause 4. The orthopaedic knee implant of any one of clauses 1-3, wherein the second layer comprises a first zirconium nitride sublayer and at least nine alternating sublayers of niobium nitride sublayers, zirconium sublayers, and zirconium nitride sublayers.

Clause 5. The orthopaedic knee implant of any one of clauses 1-4, wherein the tetragonal zirconium oxide layer extends between and interconnects the monoclinic zirconium oxide layer and the second layer.

Clause 6. The orthopaedic knee implant of any one of clauses 1-5, wherein the third layer has a thickness of about 2 µm to about 5 µm.

Clause 7. The orthopaedic knee implant of any one of clauses 1-6, wherein the tetragonal zirconium oxide layer has a thickness of about 200 nm to about 3 µm.

Clause 8. The orthopaedic knee implant of any one of clause 1-7, wherein the monoclinic zirconium oxide layer has a thickness of about 200 nm to about 3 µm.

Clause 9. The orthopaedic knee implant of any one of clauses 1-8, wherein the second layer has a thickness of about 3 µm to about 6 µm.

Clause 10. The orthopaedic knee implant of any one of clauses 1-9, wherein the second layer comprises zirconium nitride sublayers each having a thickness of about 10 nm to about 200 nm.

Clause 11. The orthopaedic knee implant of any one of clauses 4-10, wherein each zirconium nitride sublayer comprises at least about 95% zirconium nitride.

Clause 12. The orthopaedic knee implant of any one of clauses 1-11, wherein the second layer comprises niobium nitride sublayers each having a thickness of about 10 nm to about 200 nm.

Clause 13. The orthopaedic knee implant of any one of clause 4-12, wherein each niobium nitride sublayer comprises at least about 95% niobium nitride.

Clause 14. The orthopaedic knee implant of any one of clauses 1-13, wherein the second layer comprises zirconium sublayers each having a thickness of about 10 nm to about 200 nm.

Clause 15. The orthopaedic knee implant of any one of clauses 4-14, wherein each zirconium sublayer comprises at least about 95% zirconium.

Clause 16. The orthopaedic knee implant of any one of clauses 1-14, wherein the first layer comprises at least about 90% zirconium.

Clause 17. The orthopaedic knee implant of any one of clauses 1-16, wherein the first layer has a thickness of about 50 nm to about 1 µm, or about 1 µm to about 3 µm.

Clause 18. The orthopaedic knee implant of any one of clauses 1-17, wherein the femoral component comprises a bone-engaging layer disposed on the bone-facing surface.

Clause 19. The orthopaedic knee implant of clause 18, wherein the bone-engaging layer is porous.

Clause 20. A process for forming a femoral component of an orthopaedic knee implant, the process comprising: i) depositing a first layer comprising zirconium on a condylar surface of a titanium substrate, wherein the condylar surface is curved in a sagittal plane; ii) depositing a number of alternating sublayers to form a second layer; and iii) depositing a third sublayer comprising zirconium nitride onto the second layer.

Clause 21. The process of clause 20, wherein the second depositing step comprises depositing a zirconium sublayer.

Clause 22. An orthopaedic knee implant comprising: a femoral component configured to be coupled to a distal end of a patient's femur, the femoral component comprising (i) a substrate comprising a titanium alloy having (a) a condylar surface that is curved in a sagittal plane and (b) a bone-facing surface positioned opposite the condylar surface; and (ii) a coating disposed on the condylar surface, the coating comprising (a) a first layer comprising niobium, zirconium, titanium, tantalum, platinum, molybdenum, alloys thereof, or combinations thereof, (b) a second layer comprising a number of alternating sublayers, and (c) a third layer comprising oxidized zirconium, wherein (i) the first layer extends between and interconnects the second layer and the condylar surface, (ii) the second layer extends between and interconnects the first layer and the third layer, and (iii) the third layer forms an outer surface of the coating.

Clause 23. The implant of clause 22, wherein the second layer comprises at least eight alternating sublayers of zirconium nitride and niobium nitride.

Clause 24. The implant of clause 23, wherein each zirconium nitride sublayer of the alternating sublayers has a thickness of about 5 nm to about 200 nm.

Clause 25. The implant of any one of clause 22-24, wherein the second layer has a thickness of about 3 µm to about 6 µm.

Clause 26. The implant of any one clauses 22-25, wherein the third layer comprises at least about 90% monoclinic oxidized zirconium.

Clause 27. The implant of any one of clauses 22-26, wherein the third layer has a thickness of about 100 nm to about 5 µm.

Clause 28. The implant of any one of clauses 22-27, wherein at least one sublayer of the second layer comprises at least about 95% zirconium nitride.

Clause 29. The implant of any one of clauses 22-28, wherein at least one sublayer of the second layer has a thickness of about 5 nm to about 500 nm.

Clause 30. The implant of any one of clauses 22-29, wherein at least one sublayer of the second layer comprises at least about 95% niobium nitride.

Clause 31. The implant of any one of clauses 22-30, wherein the first layer comprises at least about 90% zirconium.

Clause 32. The implant of any one of clauses 22-31, wherein the first layer has a thickness of about 50 nm to about 1 µm.

Clause 33. The implant of any one of clauses 22-32, wherein the femoral component comprises a bone-engaging layer disposed on the bone-facing surface.

Clause 34. The implant of clause 33, wherein the bone-engaging layer is porous.

Clause 35. The implant of any one of clauses 22-34, wherein the second layer comprises an inner sublayer and an outer sublayer.

Clause 36. The implant of clause 35, wherein the inner sublayer and the outer sublayer have the same composition.

Clause 37. The implant of any one of clauses 35-36, wherein the second layer comprises an intermediate sublayer having a composition different from the inner sublayer, the outer sublayer, or both.

Clause 38. A process for forming a femoral component of an orthopaedic knee implant, the process comprising: depositing a first layer comprising niobium, zirconium, titanium, tantalum, platinum, molybdenum, an alloy thereof, or combinations thereof on a condylar surface of a substrate comprising titanium, wherein the condylar surface is curved in a sagittal plane; and depositing a second layer comprising a number of alternating sublayers.

Clause 39. The process of clause 38, comprising oxidizing a portion of the second layer to form a third layer.

Clause 40. The process of any one of clauses 38-39, wherein the alternating sublayers comprise a sublayer of zirconium nitride and a sublayer of niobium nitride.

Clause 41. The process of any one of clauses 38-40, comprising depositing a third layer on an outer surface of the second layer.

Clause 42. The process of clause 41, wherein the third layer comprises zirconium nitride, titanium zirconium nitride, zirconium oxide, niobium oxide, zirconium oxynitride, niobium oxynitride, or a combination thereof.

Clause 43. An orthopaedic knee implant comprising: a femoral component configured to be coupled to a distal end of a patient's femur, the femoral component comprising (i) a substrate comprising a titanium alloy having (a) a condylar surface that is curved in a sagittal plane and (b) a bone-facing surface positioned opposite the condylar surface; and (ii) an coating disposed on the condylar surface, the coating comprising (a) a first layer comprising niobium, zirconium, titanium, tantalum, platinum, molybdenum, alloys thereof, or combinations thereof, (b) a second layer comprising a number of alternating sublayers grouped together in bilayers or trilayers, and (c) a third layer comprising oxidized zirconium, wherein (i) the first layer extends between and interconnects the second layer and the condylar surface, (ii) the second layer extends between and interconnects the first layer and the third layer, and (iii) the third layer forms an outer surface of the coating.

Clause 44. The implant of clause 43, wherein the second layer comprises at least 12 bilayers and wherein each sublayer within a bilayer has a similar thickness.

Clause 45. The implant of clause 44, wherein each sublayer has a thickness of about 5 nm to about 200 nm.

Clause 46. The implant of any one of clause 43-45, wherein the second layer has a thickness of about 3 µm to about 8 µm.

Clause 47. The implant of any one of clauses 43-46, wherein the third layer comprises at least about 90% monoclinic oxidized zirconium.

Clause 48. The implant of any one of clauses 43-47, wherein the third layer has a thickness of about 100 nm to about 5 µm.

Clause 49. The implant of clause 43, wherein the second layer comprises at least 8 trilayers and wherein each sublayer within a trilayer has a similar thickness.

Clause 50. The implant of clause 49, wherein each sublayer has a thickness of about 5 nm to about 500 nm.

Clause 51. The implant of clause 43, wherein the second layer comprises at least 12 bilayers and wherein each sublayer within a bilayer has a different thickness, and wherein all bilayers have a uniform thickness.

Clause 52. The implant of clause 43, wherein the second layer comprises at least 8 trilayers and wherein each sublayer within a trilayer has a different thickness, and wherein all trilayers have a uniform thickness.

Clause 53. The implant of any one of clauses 43-52, wherein the first layer has a thickness of about 50 nm to about 1 µm or 100 nm to 2 µm.

Clause 54. The implant of any one of clauses 43-53, wherein the femoral component comprises a bone-engaging layer disposed on the bone-facing surface.

Clause 55. The implant of clause 54, wherein the bone-engaging layer is porous.

Clause 56. The implant of clause 51, wherein each bilayer includes a first sublayer and a second sublayer, and the first sublayer has a thickness that decreases between 1% and 20% in each subsequent bilayer, and the second sublayer has a thickness that increases between 1% and 20% in each subsequent bilayer.

Clause 57. The implant of clause 56, wherein the first sublayer makes up at least 55% of the second layer.

Clause 58. The implant of any one of clauses 43-57, wherein the second layer comprises a metal sublayer selected from the group consisting of niobium, zirconium, titanium, tantalum, platinum, molybdenum, alloys thereof, and combinations thereof; a ceramic sublayer comprising niobium, zirconium, titanium, tantalum, molybdenum, platinum, or combinations thereof; and a third layer selected from the group consisting of zirconium oxide, niobium oxide, zirconium oxynitride, niobium oxynitride, titanium nitride, titanium zirconium nitride, and combinations thereof.

Clause 59. The implant of clause 43, wherein the third layer comprises titanium zirconium nitride.

Clause 60. A process for forming a femoral component of an orthopaedic knee implant, the process comprising: depositing a first layer comprising niobium, zirconium, titanium, tantalum, platinum, molybdenum, or combinations thereof on a condylar surface of a substrate comprising titanium, wherein the condylar surface is curved in a sagittal plane; and depositing a number of alternating sublayers to form a second layer.

Clause 61. The process of clause 60, comprising oxidizing a portion of the second layer to form a third layer comprising oxidized zirconium.

Clause 62. The process of clause 61, wherein the alternating sublayers comprise a sublayer of zirconium nitride and a sublayer of niobium nitride.

Clause 63. The process of any one of clauses 60-62, comprising depositing a third layer on an outer surface of the second layer.

Clause 64. The process of clause 63, wherein the third layer comprises zirconium nitride, titanium zirconium nitride, zirconium oxide, niobium oxide, zirconium oxynitride, niobium oxynitride, or a combination thereof.

Clause 65. An orthopaedic knee implant comprising: a femoral component configured to be coupled to a distal end of a patient's femur, the femoral component comprising: (i) a substrate comprising a titanium alloy having (a) a condylar surface that is curved in a sagittal plane and (b) a bone-facing surface positioned opposite the condylar surface; and (ii) a coating disposed on the condylar surface, the coating comprising (a) a first layer comprising niobium, zirconium, titanium, tantalum, platinum, molybdenum, alloys thereof, or combinations thereof, (b) an outer ceramic third layer, and (c) a plurality of alternating sublayers positioned between and interconnecting the first layer and the outer ceramic third layer, wherein (i) the plurality of alternating sublayers are configured to resist crack propagation from the outer ceramic third layer, the plurality of alternating sublayers include a number of metallic sublayers and a number of ceramic sublayers that are harder than the metallic sublayers, and (ii) the outer ceramic third layer forms an outer articular surface of the femoral component and is shaped to contact a concave proximal surface of a tibial bearing.

Clause 66. The orthopaedic knee implant of any one of clauses 1-19, 22-37, 43-59 (but not clauses 49 or 52), and 65, wherein a first sublayer and a second sublayer form a bilayer comprising niobium and zirconium nitride, and the third layer comprises zirconium nitride.

Clause 67. The orthopaedic knee implant of any one of clauses 1-19, 22-37, 43-59 (but not clauses 49 or 52), and 65, wherein a first sublayer and a second sublayer form a bilayer comprising niobium and zirconium nitride, and the third layer comprises titanium zirconium nitride.

Clause 68. The orthopaedic knee implant of any one of clauses 1-19, 22-37, 43-59 (but not clauses 49 or 52), and 65, wherein a first sublayer and a second sublayer form a bilayer comprising zirconium nitride and zirconium, and the third layer comprises zirconium nitride.

Clause 69. The orthopaedic knee implant of any one of clauses 1-19, 22-37, 43-59 (but not clauses 49 or 52), and 65, wherein a first sublayer and a second sublayer form a bilayer comprising zirconium nitride and zirconium, and the third layer comprises titanium zirconium nitride.

Clause 70. The orthopaedic knee implant of any one of clauses 1-19, 22-37, 43-59 (but not clauses 49 or 52), and 65, wherein a first sublayer and a second sublayer form a bilayer comprising zirconium titanium and titanium zirconium nitride, and the third layer comprises titanium zirconium nitride.

Clause 71. The orthopaedic knee implant of any one of clauses 1-19, 22-37, 43-59 (but not clauses 49 or 52), and 65-70, wherein the third layer comprises zirconium nitride.

Clause 72. The orthopaedic knee implant of any one of clauses 1-19, 22-37, 43-59 (but not clauses 49 or 52), and 65-70, wherein the third layer comprises titanium zirconium nitride.

Clause 73. The orthopaedic knee implant of any one of clauses 1-19, 22-37, 43-59 (but not clauses 49 or 52), and 65-70, wherein the intermediate layer includes a plurality of alternating titanium zirconium nitride sublayer and zirconium titanium alloy metal sublayer.

Clause 74. The orthopaedic knee implant of any one of clauses 1-19, 22-37, 43-59 (but not clauses 49 or 52), and 65-70, wherein the intermediate layer includes a plurality of alternating zirconium nitride sublayer and zirconium titanium alloy sublayer.

Clause 75. The orthopaedic knee implant of any one of clauses 1-19, 22-37, 43-59 (but not clauses 49 or 52), and 65-70, wherein the third layer comprises ceramic.

Clause 76. The orthopaedic knee implant of any one of clauses 1-19, 22-37, 43-59, and 65-75, wherein the plurality of alternating sublayers are grouped by bilayers or trilayers.

Clause 77. The orthopaedic knee implant of clause 76, wherein each bilayer or each trilayer have a uniform thickness to the other grouped sublayers in the intermediate layer, but the individual thickness of each sublayer within the grouping is varied.

Clause 78. The orthopaedic knee implant any one of clauses 1-19, 22-37, 43-59, and 65-77, wherein the third layer is titanium zirconium nitride.

Clause 79. The orthopaedic knee implant of clause 78, wherein the atomic percent of zirconium in the third layer is 50 At % to 80 At %.

Clause 80. The orthopaedic knee implant of clause 78, wherein the atomic percent of zirconium in the third layer is 30 At % to 85 At %.

Clause 81. The orthopaedic knee implant of clauses 1-19, 22-37, 43-59, and 65-80, wherein the plurality of alternating sublayers include a number of titanium zirconium nitride sublayers and a number of metallic layers.

Clause 82. The orthopaedic knee implant of clauses 81, wherein the atomic percent of zirconium in the plurality of alternating sublayers is 30 At % to 85 At %.

Clause 83. The orthopaedic knee implant of clauses 81, wherein the atomic percent of zirconium-titanium alloy in the plurality of alternating sublayers is 30 At % to 85 At %.

BRIEF DESCRIPTION

The detailed description particularly refers to the following figures, in which:

FIG. 10 is an illustrative view of an embodiment of a femoral component;

FIG. 11 is an illustrative view of an embodiment of a femoral component;

FIG. 12 is an illustrative view of an embodiment of a femoral component;

FIG. 13 is an illustrative view of an embodiment of a femoral component;

FIG. 14 is an illustrative view of an embodiment of a femoral component;

FIG. 15 is an illustrative view of an embodiment of a femoral component;

DETAILED DESCRIPTION

Figure 1:
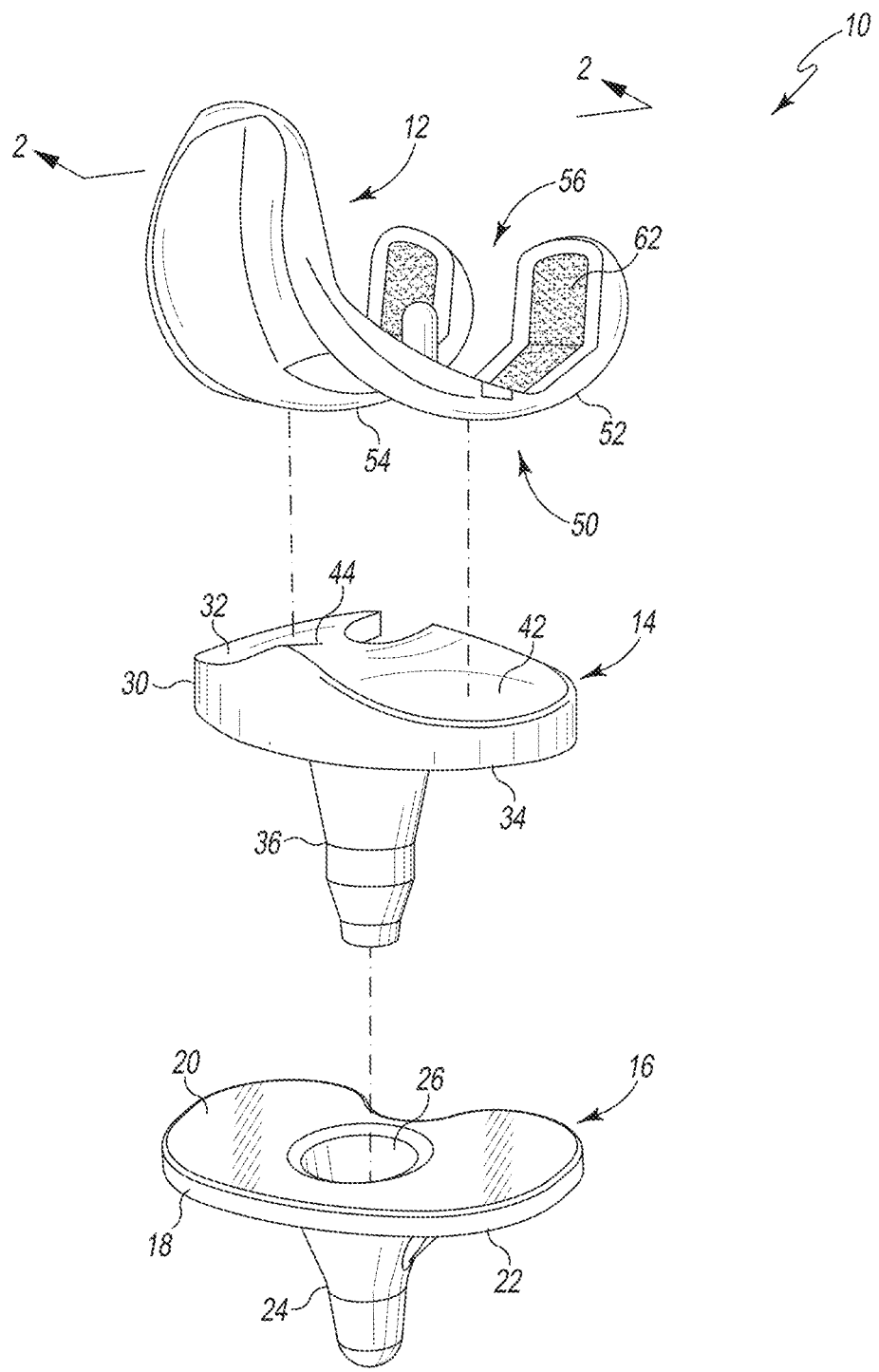
FIG. 1 is an exploded perspective view of an orthopaedic knee prosthesis, showing a femoral component, a tibial bearing, and a tibial tray.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or orthopaedic prostheses described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, in one embodiment, an orthopaedic knee prosthesis 10 includes a femoral component 12, a tibial bearing 14, and a tibial tray 16. The femoral component 12 is configured to articulate with the tibial bearing 14, which is configured to be coupled with the tibial tray 16. In the illustrative embodiment of FIG. 1, the tibial bearing 14 is embodied as a rotating or mobile tibial bearing and is configured to rotate relative to the tibial tray 16 during use. However, in other embodiments, the tibial bearing 14 may be embodied as a fixed tibial bearing, which may be limited or restricted from rotating relative to the tibial tray 16.

The tibial tray 16 is configured to be secured to a surgically-prepared proximal end of a patient's tibia (not shown). The tibial tray 16 may be secured to the patient's tibia via use of bone cement or other attachment methods. The tibial tray 16 includes a platform 18 having a top surface 20 and a bottom surface 22. Illustratively, the top surface 20 is generally planar. The tibial tray 16 also includes a stem 24 extending downwardly from the bottom surface 22 of the platform 18. A cavity or bore 26 is defined in the top surface 20 of the platform 18 and extends downwardly into the stem 24. The bore 26 is formed to receive a complimentary stem 36 of the tibial bearing 14 as discussed in more detail below.

As discussed above, the tibial bearing 14 is configured to be coupled with the tibial tray 16. The tibial bearing 14 includes a platform 30 having an upper bearing surface 32 and a bottom bearing surface 34. In the illustrative embodiment wherein the tibial bearing 14 is embodied as a rotating or mobile tibial bearing, the bearing 14 includes a stem 36 extending downwardly from the bottom surface 34 of the platform 30. When the tibial bearing 14 is coupled to the tibial tray 16, the stem 36 is received in the bore 26 of the tibial tray 16. In use, the tibial bearing 14 is configured to rotate about an axis defined by the stem 36 relative to the tibial tray 16. In embodiments wherein the tibial bearing 14 is embodied as a fixed tibial bearing, the bearing 14 may or may not include the stem 36 and/or may include other devices or features to secure the tibial bearing 14 to the tibial tray 16 in a non-rotating configuration.

The upper bearing surface 32 of the tibial bearing 14 includes a medial bearing surface 42 and a lateral bearing surface 44. The medial and lateral bearing surfaces 42, 44 are configured to receive or otherwise contact corresponding medial and lateral condyles 52, 54 of the femoral component 12 as discussed in more detail below. As such, each of the bearing surfaces 42, 44 has a concave contour.

The femoral component 12 is configured to be coupled to a surgically-prepared surface of the distal end of a patient's femur (not shown). The femoral component 12 may be secured to the patient's femur via use of bone adhesive or other attachment methods. The femoral component 12 includes a pair of medial and lateral condyles 52, 54. The condyles 52, 54 are spaced apart to define an intracondyle notch 56 therebetween. In use, the condyles 52, 54 replace the natural condyles of the patient's femur and are configured to articulate on the corresponding bearing surfaces 42, 44 of the platform 30 of the tibial bearing 14.

The illustrative orthopaedic knee prosthesis 10 (sometime referred to as an "implant") of FIG. 1 is embodied as a posterior cruciate-retaining knee prosthesis. That is, the femoral component 12 is embodied as a posterior cruciate-retaining knee prosthesis and the tibial bearing 14 is embodied as a posterior cruciate-retaining tibial bearing 14. However, in other embodiments, the orthopaedic knee prosthesis 10 may be embodied as a posterior cruciate-sacrificing knee prosthesis.

Figure 2:
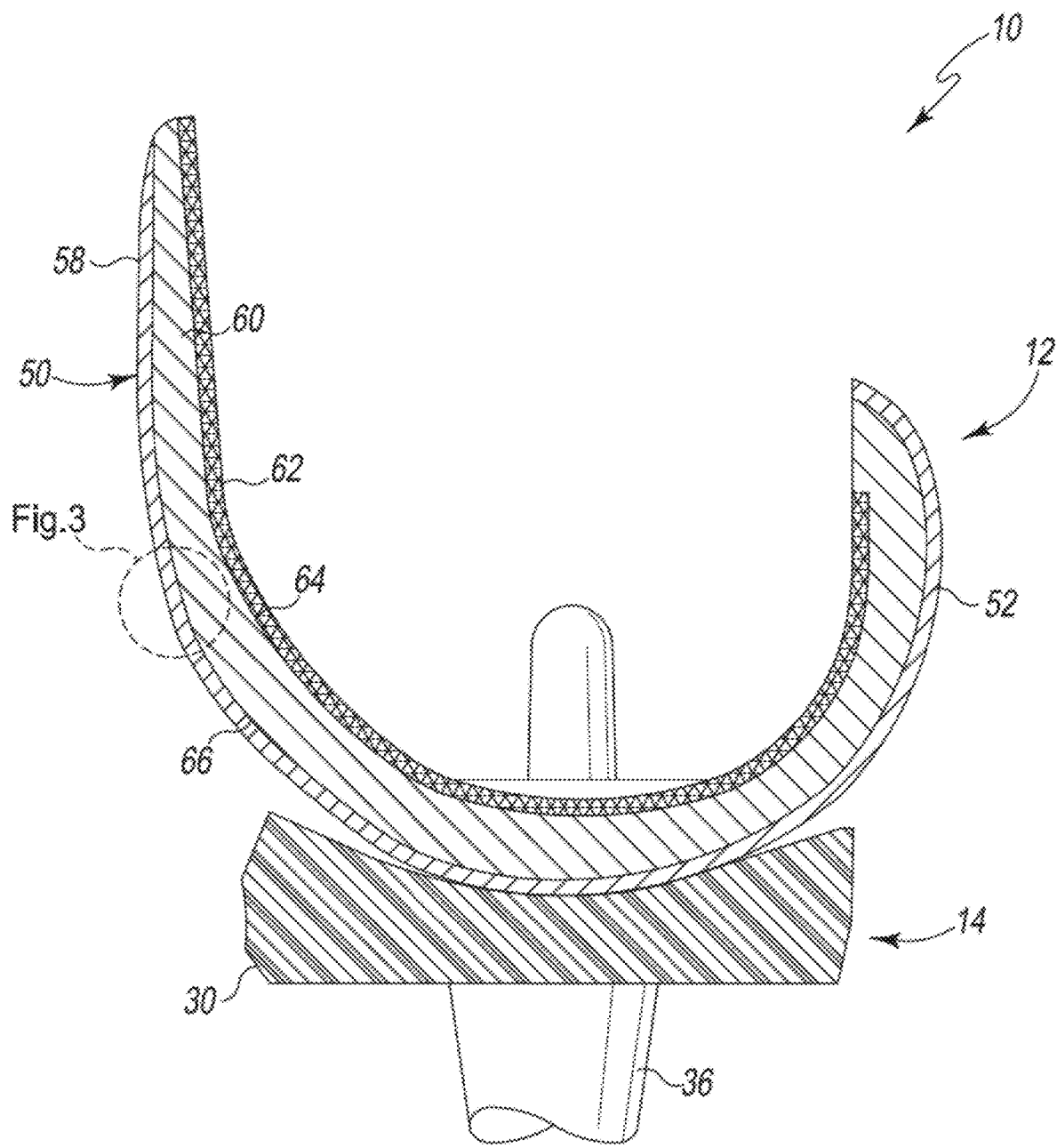
FIG. 2 is a cross-sectional view of the femoral component and the tibial bearing of FIG. 1 along the sagittal plane, taken generally along line 2-2 of FIG. 1, as viewed in the direction of the arrows, note the porous-metal coating is not shown in cross section in FIG. 2 for clarity of description.

Referring now to FIGS. 1 and 2, the femoral component 12 is configured to articulate on the tibial bearing 14 during use. Each condyle 52, 54 of the femoral component 12 includes an outer articular surface 50, which is convexly curved in the sagittal plane and configured to face the respective bearing surface 42, 44 of the tibial bearing 14.

As shown in FIG. 2, the femoral component 12 includes a substrate 60 and a coating 58. Illustratively, the coating 58 is disposed on the substrate 60 and is configured to interact with the tibial bearing 14. In some embodiments, the femoral component 12 includes a bone-engaging layer 62 located opposite the coating 58 to locate the substrate 60 therebetween. The bone-engaging layer 62 is configured to interact with a surgically prepared femur of a patient.

The substrate 60 comprises a condylar surface 66 and a bone-facing surface 64, as shown in FIG. 2. The condylar surface 66 is curved in a sagittal plane and is configured to locate the coating 58 on the substrate 60. The bone-facing surface 64 is positioned opposite the condylar surface 66 and is arranged to face a surgically-prepared distal end of a patient's femur. In some embodiments, the bone-facing surface 64 contacts the surgically-prepared femur bone directly. In some embodiments, a bone-engaging layer 62 is coupled to the bone-facing surface 64 of the substrate 60.

FIGS. 1 and 2 show a cementless embodiment of the femoral component 12 where the bone-engaging layer 62 is configured to be implanted in the absence of cement between the femoral component 12 and the surgically-prepared distal end of a patient's femur. In some embodiments, the bone-engaging layer 62 comprises titanium. It should be appreciated that the bone-engaging layer 62 could be a separately-applied coating such as Porocoat® Porous Coating, which is commercially available from DePuy Synthes of Warsaw, Ind.

In some embodiments, the bone-engaging layer 62 can be defined by a porous three-dimensional structure formed by a plurality of interconnected struts. In one example, the plurality of interconnected struts form a plurality of geometric structures, which, in the illustrative embodiment, are rhombic trigonal trapezohedrons. It should be appreciated that such geometric structures may vary to fit the needs of a given design. Further, it should be appreciated that the bone-engaging layer 62 may be formed from any other alternative geometry suitable to fit the needs of a given design.

In some embodiments, the bone-engaging layer 62 is formed from a metal powder. Illustratively, the metal powder may include, but are not limited to, titanium, titanium alloys, stainless steel, cobalt chrome alloys, tantalum, niobium, or a combination thereof. The bone-engaging layer 62 has a porosity suitable to facilitate bony ingrowth into the bone-engaging layer 62 of the femoral component 12 when implanted into the surgically-prepared surface of the distal end of a patient's femur.

In the illustrative embodiment described herein, the bone-engaging layer 62 is additively manufactured directly onto the bone-facing surface 64 of the femoral component 12. In such an embodiment, the two structures—i.e., the femoral component 12 and bone-engaging layer 62—may be manufactured contemporaneously during a common additive manufacturing process. For example, the two structures may be manufactured contemporaneously in a single 3D printing operation that yields a common, monolithic metallic component including both structures. Alternatively, the bone-engaging layer 62 could be manufactured as a separate component that is secured to the bone-facing surface 64 of the femoral component 12.

In alternative embodiments, the femoral component 12 is configured to attach to the surgically-prepared distal end of a patient's femur using cement. In some embodiments, the femoral component 12 comprises a cement reservoir (not shown) disposed on the bone-facing surface 64. In some embodiments, the bone adhesive is disposed on the bone-facing surface 64. In some embodiments, the bone adhesive comprises bone cement. In some embodiments, the bone-facing surface 64 is configured to receive a bone adhesive.

In some embodiments, the substrate 60 is metallic. In some embodiments, the substrate 60 comprises a metal alloy. In some embodiments, the substrate 60 comprises a titanium alloy. In some embodiments, the substrate 60 comprises titanium and vanadium. In some embodiments, the substrate 60 comprises titanium, aluminum, and vanadium. In some embodiments, the substrate 60 comprises Ti-6Al-4V. In some embodiments, the substrate 60 consists essentially of Ti-6Al-4V.

Figure 3:
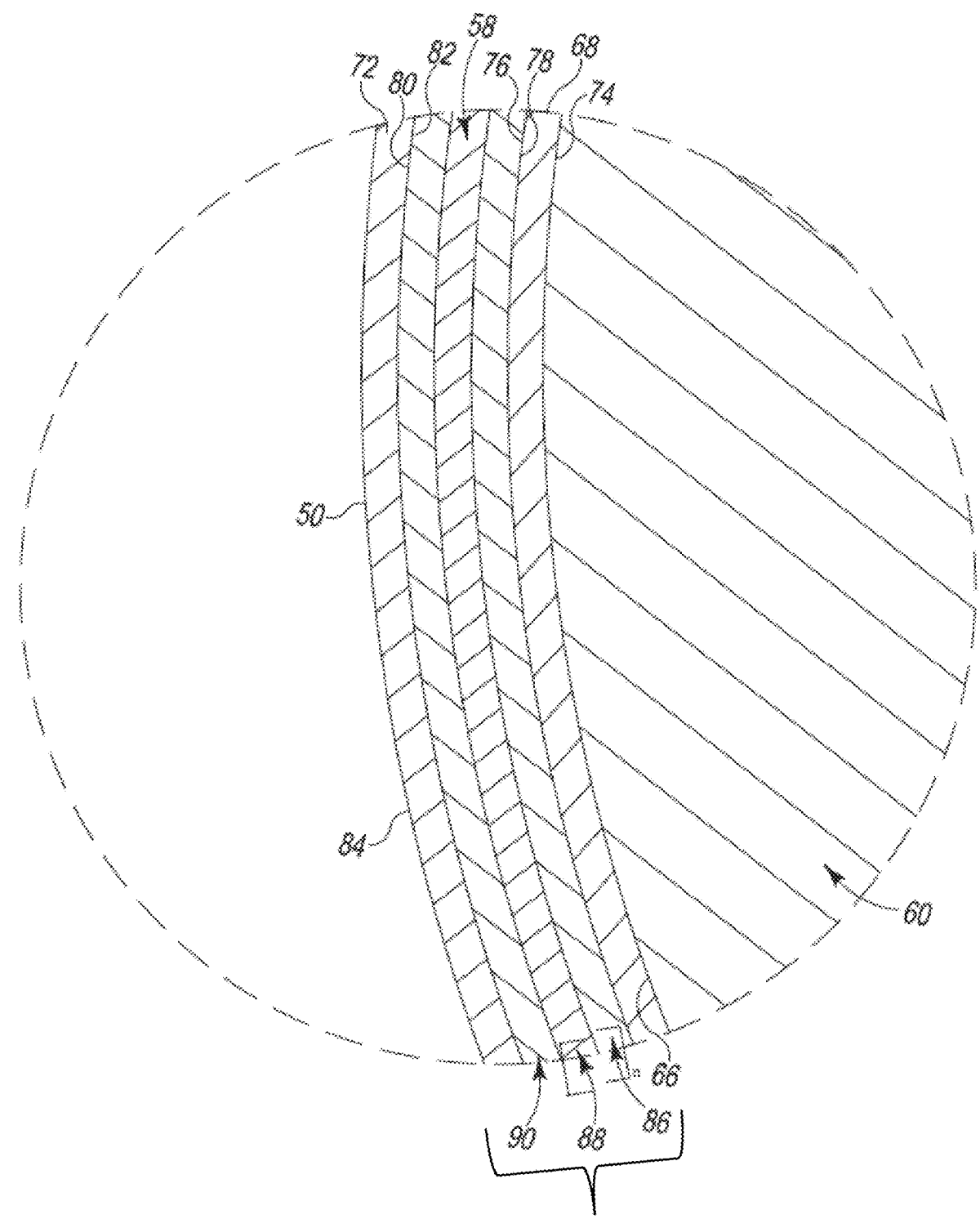
FIG. 3 is an enlarged cross-sectional view taken from FIG. 2 as indicated by the encircled area.

Referring now to FIGS. 2 and 3, the coating 58 is disposed on the condylar surface 66. The coating 58 is located opposite the bone-facing surface 64 to locate the substrate 60 therebetween. The coating 58 is configured to interact with the bearing surfaces 42, 44 and to articulate with the tibial bearing 14.

The coating 58 has a number of layers 68, 70, 72. The layers 68, 70, 72 may each be constructed with a material which possesses mechanical properties favorable for use in the construction of the coating 58 (e.g., enhanced wear resistance, resists chipping, resists delamination, tunable stiffness, ductile, corrosion resistance, and oxidation resistance).

In some embodiments, the coating 58 cooperates with the substrate 60 to minimize scratching of the outer articular surface 50 of the femoral component 12. In some embodiments, the coating 58 cooperates with the substrate 60 to minimize cohesive chipping and delamination of the coating 58. In some embodiments, the coating 58 cooperates with the substrate 60 to resist corrosion. In some embodiments, the coating 58 provides density and toughness. In some embodiments, the coating 58 cooperates with the substrate 60 to provide sufficient toughness to minimize or avoid fracturing.

Referring now to FIG. 3, the coating 58 comprises an inner or bonding layer 68, an intermediate layer 70, and an outer layer 72. The outer layer 72, the intermediate layer 70, or both the outer layer 72 and the intermediate layer 70 of the coating 58 is constructed with a material which possesses mechanical properties favorable for use in the construction of the coating 58. For example, the intermediate layer 70 is constructed with materials that provide a stiffness and ductility that spread the load of a force, arrest cracking, and improve adhesion of the coating 58 to the substrate 60. The bonding layer 68, on the other hand, is constructed of a material which possesses mechanical properties favorable for use in securing the coating 58 to the substrate 60.

It should be appreciated that, as used herein, the term "layer" is not intended to be limited to a "thickness" of material positioned proximate to another similarly dimensioned "thickness" of material, but rather is intended to include numerous structures, configurations, and constructions of material. For example, the term "layer" may include a portion, region, or other structure of material which is positioned proximate to another portion, region, or structure of differing material. For example, although the interface between the intermediate layer 70 and the outer layer 72 is shown to be uniform in FIG. 3, in some embodiments the interface is irregular such that the intermediate layer 70 and the outer layer 72 do not have a uniform thickness. In some embodiments, a "layer" is formed by modifying a surface or a portion of an existing layer. For example, in some embodiments, the outer layer 72 is formed from oxidizing an outer portion of the intermediate layer 70. In alternative embodiments, a "layer" is formed by providing additional material to an existing surface. For example, in some embodiments, the bonding layer 68 is formed by depositing a material onto the condylar surface 66.

As shown in FIG. 3, the bonding layer 68 is disposed on the condylar surface 66. The outer layer 72 is arranged to form the outer articular surface 50 of the coating 58 and hence the femoral component 12. The intermediate layer 70 extends between and interconnects the bonding layer 68 and the outer layer 72. In some embodiments, the coating 58 does not include an outer layer 72 (as shown in FIG. 11) such that an exposed surface of the intermediate layer 70 may be further processed to form the outer articular surface 50.

The bonding layer 68 extends between and interconnects the intermediate layer 70 and the condylar surface 66. The inner layer 68 includes an inner surface 74 and an outer surface 76. The inner surface 74 is located between the outer surface 76 and the condylar surface 66. The outer surface 76 of the inner layer 68 is located between the inner surface 74 of the inner layer 68 and the intermediate layer 70. In some embodiments, the inner layer 68 is configured to reduce delamination of the coating 58 from the femoral component 12.

The bonding layer 68 may have a particular thickness as measured from the condylar surface 66. In some embodiments, the bonding layer 68 may be present at a thickness in the nanoscale to the micron scale. In some embodiments, the bonding layer 68 has a thickness of about 0.5 nm to about 10 nm, about 0.5 nm to about 3 nm, or about 5 nm to about 10 nm. In some embodiments, the bonding layer 68 has a thickness of about 0.10 µm to about 2 µm. In some embodiments, the bonding layer 68 has a thickness of about 200 nm to about 1 µm. In some embodiments, the bonding layer 68 has a thickness of at least about 0.10 µm, at least about 0.20 µm, at least about 0.30 µm, at least about 0.5 µm, at least about 1 µm, at least about 1.5 µm, or at least about 2 µm. In some embodiments, the bonding layer 68 has a thickness of about 200 nm, about 220 nm, about 240 nm, about 260 nm, about 280 nm, about 300 nm, about 320 nm, about 340 nm, about 360 nm, about 38 nm, about 400 nm, about 420 nm, about 440 nm, about 460 nm, about 480 nm, about, or about 500 nm.

The bonding layer 68 may include metals, alloys, or other suitable material to provide mechanical properties favorable for use in securing the coating 58 to the substrate 60. For example, the composition of the bonding layer 68 can be selected to minimize cohesive chipping of the coating 58 during manufacturing and in use. In illustrative embodiments, the bonding layer 68 comprises niobium, zirconium, titanium, tantalum, molybdenum, platinum, hafnium, combinations thereof, or any other suitable metal. In some embodiments, the bonding layer 68 comprises zirconium. In some embodiments, the bonding layer 68 comprises at least about 90% zirconium. In some embodiments, the bonding layer 68 comprises at least about 95% zirconium. In some embodiments, the bonding layer 68 comprises at least about 90% of niobium, titanium, tantalum, molybdenum, platinum, or combinations thereof. In some embodiments, the bonding layer 68 comprises at least about 95% niobium, zirconium, titanium, tantalum, molybdenum, platinum, hafnium, or combinations thereof.

As described above, the intermediate layer 70 extends between and interconnects the bonding layer 68 and the outer layer 72. The intermediate layer 70 comprises an inner surface 78 and outer surface 80. The inner surface 78 of the intermediate layer 70 is located between the inner layer 68 and the outer surface 80 of the intermediate layer 70. The outer surface 80 of the intermediate layer 70 is located between the inner surface 78 of the intermediate layer 70 and the outer layer 72.

In some embodiments, the intermediate layer 70 has an overall thickness of about 3 µm to about 7 µm. In some embodiments, the intermediate layer 70 has an overall thickness of about 3 µm to about 8 µm. In some embodiments, the intermediate layer 70 has an overall thickness of about 5 nm to about 5 µm. In some embodiments, the intermediate layer 70 has an overall thickness of about 1.5 µm to about 2.0 µm. In some embodiments, the intermediate layer 70 has an overall thickness of at least about 50 nm, at least about 100 nm, at least about 200 nm, at least about 0.5 µm, at least about 1 µm, at least about 2 µm, at least about 3 µm, or at least about 4 µm. In some embodiments, the intermediate layer 70 has an overall thickness of about 3.2 µm, about 3.5 µm, about 4.0 µm, about 4.2 µm, about 4.3 µm, about 4.5 µm, about 5.0 µm, about 5.3 µm, about 5.5 µm, about 6.0 µm, about 6.3 µm, about 6.4 µm, or about 6.5 µm.

The intermediate layer 70 can be formed of a plurality of sublayers. The order and composition of the sublayers 86, 88, 90 are configured to disperse the load and arrest cracking that may occur. In an illustrative embodiment, the intermediate layer 70 is formed of an inner sublayer 86, an intermediate sublayer 88, and an outer sublayer 90. In some illustrative embodiments, some or all of the sublayers 86, 88, 90 repeat so that the intermediate layer 70 can include two or more of one of the sublayers.

The sublayers 86, 88, 90 can include metals, alloys, ceramics, or other suitable materials as described herein. Illustratively, the various combinations of sublayers 86, 88, or 90 provide fracture toughness and corrosion resistance. For example, each of the sublayers 86, 88, and 90 may comprise niobium, zirconium, titanium, tantalum, hafnium, molybdenum, platinum, combinations thereof, or any other suitable metal, including alloys thereof. Each of the sublayers 86, 88, and 90 may comprise a ceramic comprising niobium, zirconium, titanium, tantalum, molybdenum, platinum, combinations thereof, or any other suitable ceramic. Illustratively, a ceramic may comprise a metal and a nitride, a carbide, an oxide, or combinations thereof. For example, the ceramic may comprise zirconium nitride, titanium zirconium nitride, zirconium oxide, or niobium nitride.

In some embodiments, the number of alternating sublayers include a number of titanium zirconium nitride sublayers and a number of metallic layers. In some embodiments, the atomic percent of zirconium in the plurality of alternating sublayers is 30 At % to 85 At %. In some embodiments, the atomic percent of zirconium in the plurality of alternating sublayers is about 30 At %, about 35 At %, about 40 At %, about 45 At %, about 50 At %, about 55 At %, about 60 At %, about 65 At %, about 70 At %, about 75 At %, about 80 At %, or about 85 At %. Additionally, in some embodiments, the atomic percent of zirconium-titanium alloy in the plurality of alternating sublayers is 30 At % to 85 At %. In some embodiments, the atomic percent of zirconium-titanium alloy in the plurality of alternating sublayers is about 30 At %, about 35 At %, about 40 At %, about 45 At %, about 50 At %, about 55 At %, about 60 At %, about 65 At %, about 70 At %, about 75 At %, about 80 At %, or about 85 At %.

In illustrative embodiments, some of or all of the sublayers 86, 88, 90 may participate in a super lattice with adjacent layers or sublayers. In some embodiments, each of the sublayers 86, 88, 90 has a thickness of about 0.5 nm to about 10 nm, about 5 nm to about 10 nm, or about 0.5 nm to about 3 nm. In some embodiments, each of the sublayers 86, 88, 90 has a thickness of about 5 nm to about 500 nm.

Figure 5:
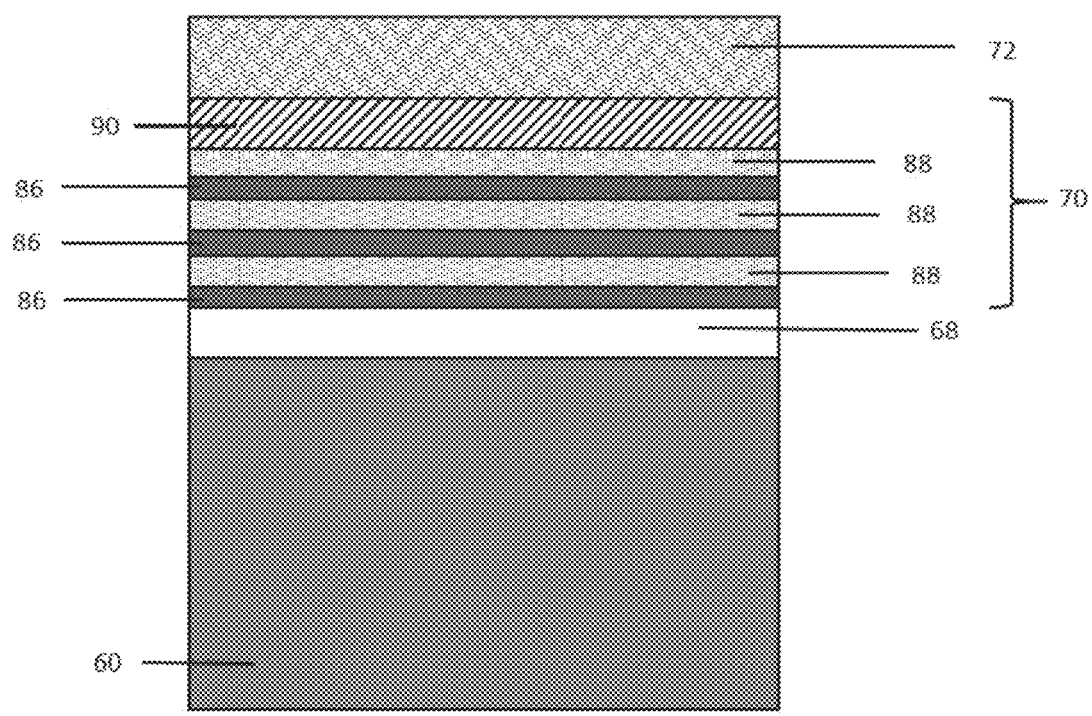
FIG. 5 is an illustrative view of an embodiment of a femoral component including a substrate, a bonding layer, an intermediate layer, and an outer layer.
Figure 6:
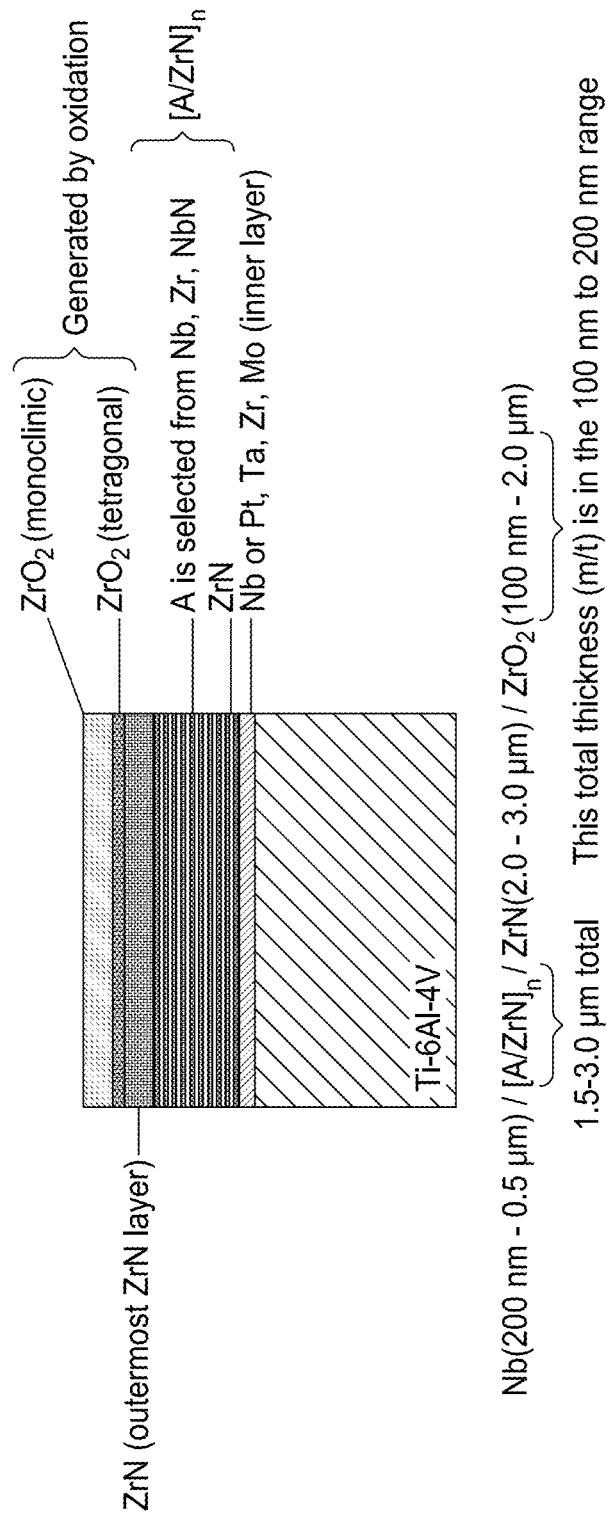
FIG. 6 is an illustrative view of an embodiment of a femoral component.
Figure 7:
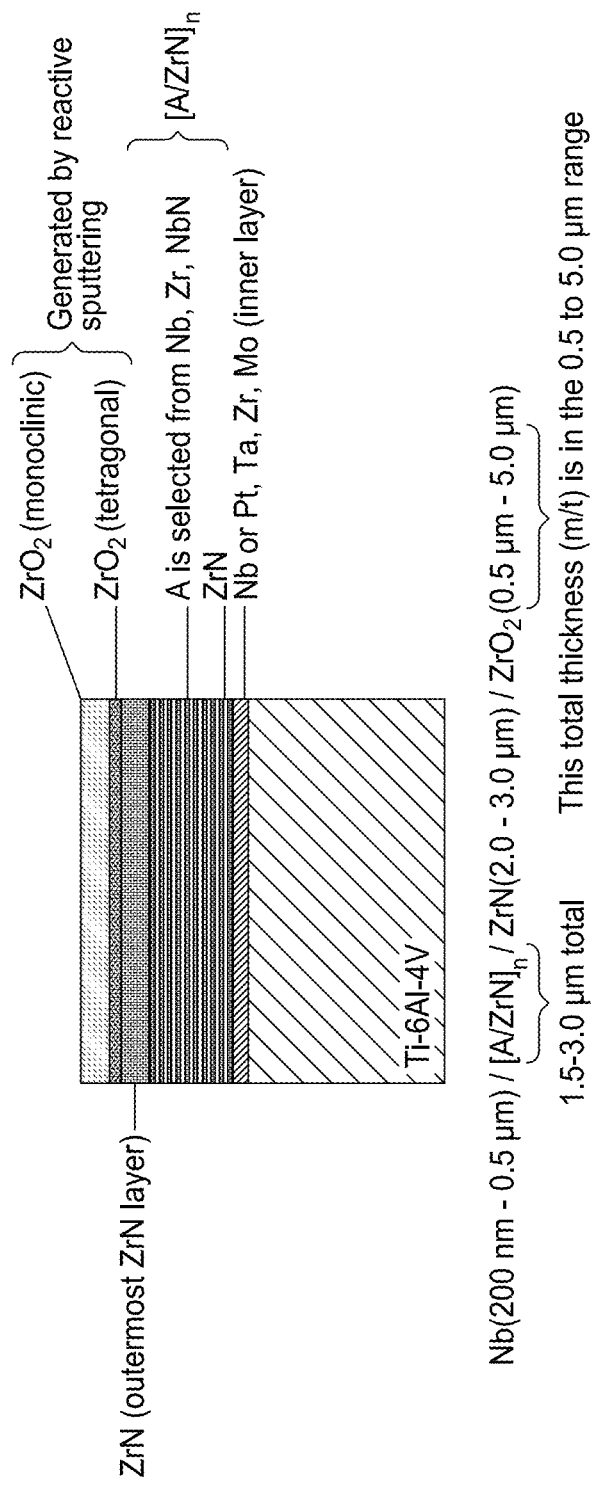
FIG. 7 is an illustrative view of an embodiment of a femoral component.
Figure 8:
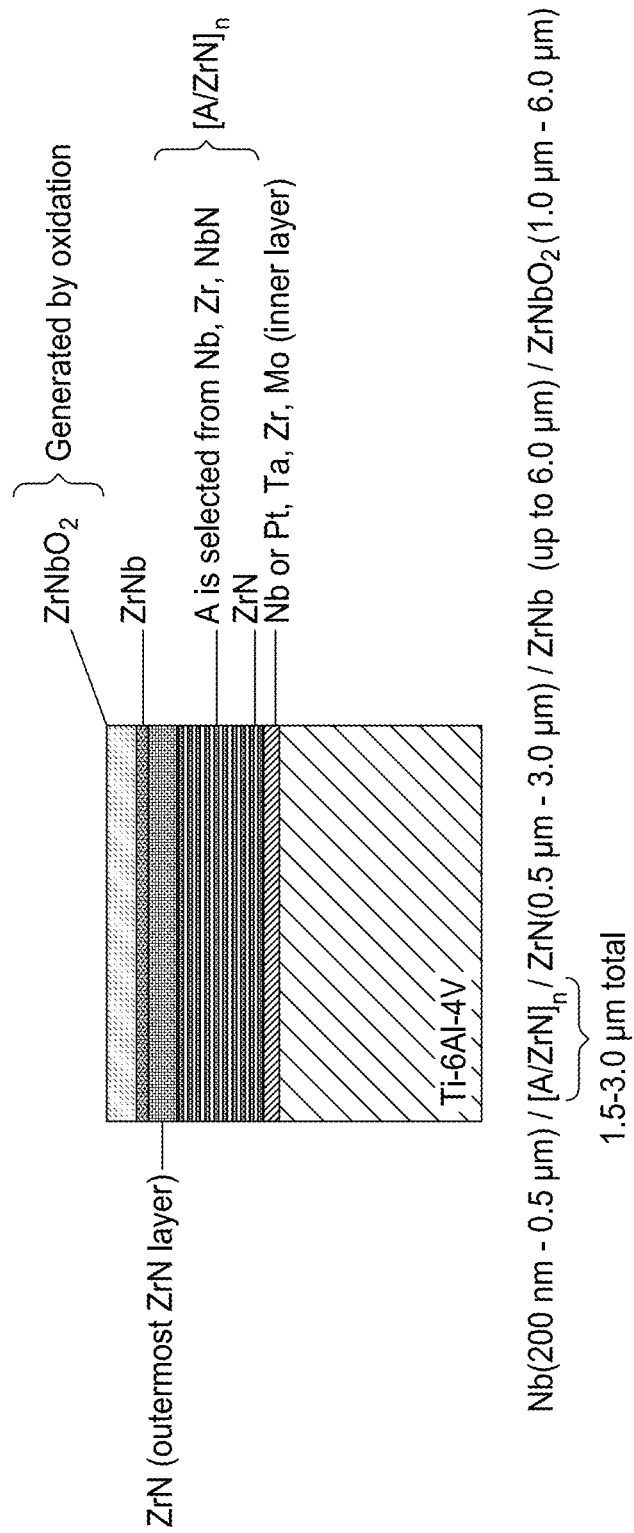
FIG. 8 is an illustrative view of an embodiment of a femoral component.
Figure 9:
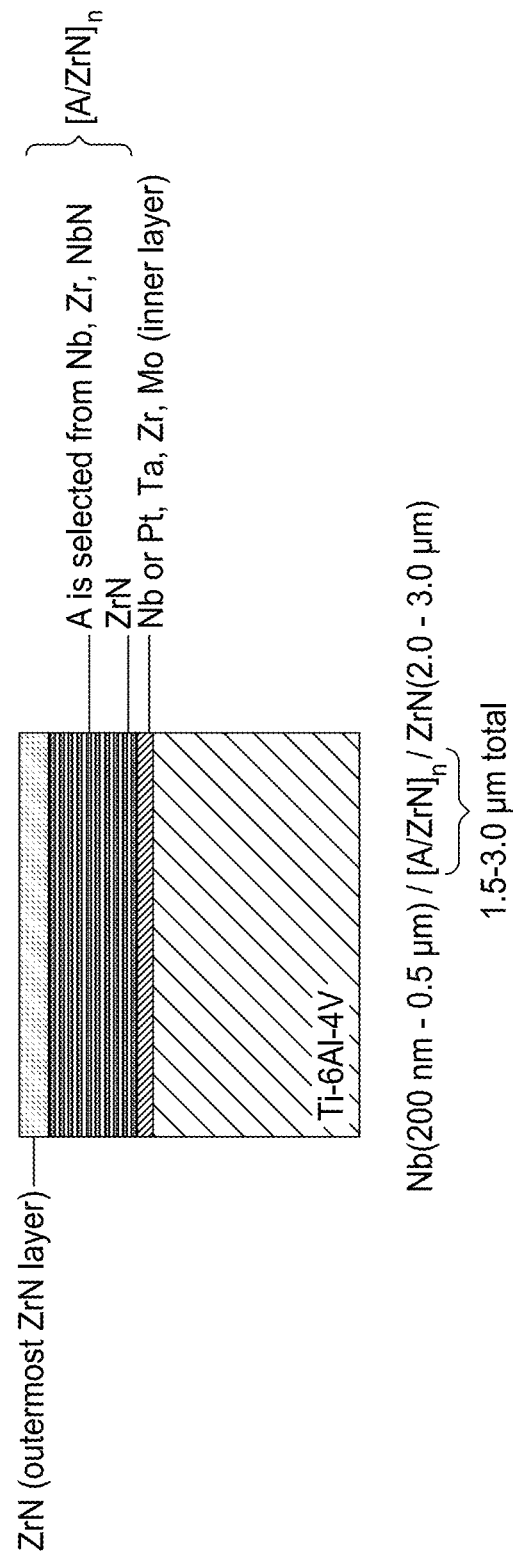
FIG. 9 is an illustrative view of an embodiment of a femoral component.

The intermediate layer 70 may comprise two different sublayers, which may be superimposed alternatingly. Referring to FIG. 5 for example, the intermediate layer 70 may comprise an inner sublayer 86, an intermediate sublayer 88, and an outer sublayer 90. The compositions of the inner sublayer 86, the intermediate sublayer 88, and the outer sublayer 90 may be the same or different. For example, the intermediate layer 70 may comprise a sequence of two sublayers, for example the inner sublayer 86 and the intermediate sublayer 88, having the composition -A-B- or (-A-B-)$_n$, where each of A and B are a different composition and n is at least 1, at least 2, at least 4, or at least 10. In this embodiment, inner sublayer 86 is A and intermediate sublayer 88 is B. Where there is a repeat of two sublayers, such as A B A B A B for example, each A-B may be referred to as a "bilayer." Accordingly, a bilayer is a grouping of two sublayers. In some embodiments, the composition of layer A comprises zirconium nitride. In some embodiments, the composition of layer B comprises niobium nitride, tantalum nitride, hafnium nitride, niobium, tetragonal and/or monoclinic zirconium, tantalum, titanium, or hafnium. In some embodiments, the number of alternating sublayers is chosen so that the intermediate layer 70 reaches an overall thickness of, for example, up to about 2 μm, up to about 4 μm, up to about 6 μm, or up to about 8 μm.

Alternatively, the intermediate layer 70 may have a sequence of two repeating sublayers, for example an inner sublayer 86 and an intermediate sublayer 88, and an outer sublayer 90, as shown in FIGS. 3 and 5. In some examples, the intermediate layer 70 includes a sequence A-(B-A)$_n$-C- including a repeating inner sublayer 86 and intermediate sublayer 88 where each of A and B are a different composition and n is at least 1, at least 2, at least 4, or at least 10, and where C is the outer sublayer 90 and has the same composition as one of the inner sublayer 86 or the intermediate sublayer 88. In some embodiments, the composition of layer A comprises zirconium nitride. In some embodiments, the composition of layer B comprises niobium nitride, tantalum nitride, hafnium nitride, niobium, tetragonal and/or monoclinic zirconium, tantalum, titanium, or hafnium. In some embodiments, the outer sublayer 90 comprises zirconium nitride. In some embodiments, the intermediate layer 70 comprises a repeating sequence of i) a sublayer of zirconium nitride, ii) a sublayer of niobium, tetragonal and/or monoclinic zirconium, tantalum, titanium hafnium, niobium nitride, tantalum nitride, or hafnium nitride, and iii) capped by an outer sublayer 90 of zirconium nitride. In some embodiments, the number of alternating sublayers is chosen so that the intermediate layer 70 reaches a thickness of, for example, up to about 5 μm.

Alternatively, the intermediate layer 70 may have a sequence of three repeating sublayers, for example, an inner sublayer 86, an intermediate sublayer 88, and an outer sublayer 90. In some examples, the intermediate layer 70 includes a repeating sequence of the inner sublayer 86, the intermediate sublayer 88, and the outer sublayer 90, having the composition -(A-B-C)$_n$- where each of A, B, and C are a different composition and n is at least 1, at least 2, at least 4, or at least 10. In this embodiment, inner sublayer 86 is A, intermediate sublayer 88 is B, and outer sublayer 90 is C. Where there is a repeat of three sublayers, such as A-B-C-A-B-C-A-B-C for example, each A-B-C may be referred to as a "trilayer." Accordingly, a trilayer is a grouping of three sublayers. It should be noted that although the formula shows a sequence of A-B-C, any permutation on the order of the sublayers is contemplated, for example A-C-B, B-C-A, etc. It should be further noted that the intermediate layer 70 may comprise more than one sequence of sublayers, for example a sequence of -A-B-C-B-C-A- and the like. It should be further noted that the intermediate layer 70 may comprise more than one sequence of sublayers, for example a sequence of -A-B-A-B-A-B-A-C-A-C-A-C and the like. It should be further noted that the intermediate layer 70 may comprise more than one sequence of sublayers, for example a sequence of -A-B-A-C-A-B-A-C-A-B-A-C and the like. Referring to FIG. 13 for example, the intermediate layer 70 may comprise a first sequence of two sublayers having the composition -A-B- or (-A-B-)$_n$ where each of A and B are a different composition and n is at least 1, at least 2, at least 4, or at least 10 and a second sequence of two sublayers having the composition -A-C- or (-A-C-)$_n$ where each of A and C are a different composition and n is at least 1, at least 2, at least 4, or at least 10. Illustratively, any of composition A, B, or C can include niobium nitride, tantalum nitride, hafnium nitride, zirconium nitride, niobium, tetragonal and/or monoclinic zirconium, tantalum, titanium, or hafnium.

In some embodiments, the intermediate layer 70 comprises a zirconium nitride inner sublayer 86, a niobium nitride intermediate sublayer 88, and a zirconium nitride outer sublayer 90. In some embodiments, the intermediate layer 70 comprises at least one zirconium nitride inner sublayer 86 and at least one niobium nitride intermediate sublayer 88. In some embodiments, the intermediate layer 70 comprises a number of alternating sublayers of zirconium nitride and niobium nitride. In some embodiments, the intermediate layer 70 comprises at least four alternating sublayers of the zirconium nitride inner sublayer 86 and the niobium nitride intermediate sublayer 88. In illustrative embodiments, the zirconium nitride outer sublayer 90 is formed on the outermost niobium nitride intermediate sublayer 88. It will be appreciated that although FIG. 3 shows a single sublayer of the zirconium nitride inner sublayer 86 and a single sublayer of the niobium nitride intermediate sublayer 88, any number of alternating sublayers is contemplated.

In some embodiments, the inner sublayer 86 has a thickness of about 5 nm to about 500 nm. In some embodiments, the inner sublayer 86 has a thickness of at least about 0.05 nm, at least about 1 nm, at least about 5 nm, at least about 10 nm, at least about 50 nm, at least about 100 nm, at least about 150 nm, at least about 200 nm, at least about 250 nm, at least about 300 nm, at least about 350 nm, at least about 400 nm, at least about 450 nm, at least about 500 nm, or at least about 550 nm. In some embodiments, the inner sublayer 86 has a thickness of about 1 nm to about 200 nm or about 5 nm to about 100 nm. In some embodiments, the sublayer 86 has a thickness of about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, or about 220 nm. In some embodiments, the sublayer 86 has a thickness of about 65 nm, about 95 nm, about 115 nm, about 125 nm or about 205 nm.

In some embodiments, the inner sublayer 86 comprises at least about 90% zirconium nitride. In some embodiments, the inner sublayer 86 comprises at least about 95% zirconium nitride.

In some embodiments, the intermediate sublayer 88 has a thickness of about 5 nm to about 500 nm. In some embodiments, the intermediate sublayer 88 has a thickness of at least about 1 nm, at least about 5 nm, at least about 10 nm, at least about 50 nm, at least about 100 nm, at least about 150 nm, or at least about 200 nm, at least about 250 nm, at least about 300 nm, at least about 350 nm, at least about 400 nm, at least about 450 nm, at least about 500 nm, or at least about 550 nm. In some embodiments, the sublayer 88 has a thickness of about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, or about 220 nm. In some embodiments, the sublayer 88 has a thickness of about 65 nm, about 95 nm, about 115 nm, about 125 nm or about 205 nm.

In some embodiments, the intermediate sublayer 88 comprises at least about 90% niobium nitride, tantalum nitride, hafnium nitride, niobium, tetragonal and/or monoclinic zirconium, tantalum, titanium, or hafnium. In some embodiments, the intermediate sublayer 88 comprises at least about 95% niobium nitride, tantalum nitride, hafnium nitride, niobium, tetragonal and/or monoclinic zirconium, tantalum, titanium, or hafnium.

In some embodiments, the outer sublayer 90 has a thickness of about 1 μm to about 5 μm. In some embodiments, the outer sublayer 90 has a thickness of about 2 μm to about 3 μm. In some embodiments, the outer sublayer 90 has a thickness of at least about 0.5 μm, at least about 1 μm, at least about 1.5 μm, at least about 2 μm, at least about 2.5 μm, at least about 3 μm, at least about 3.5 μm, at least about 4 μm, at least about 4.5 μm, at least about 5 μm, or at least about 5.5 μm. In some embodiments, the outer sublayer 90 forms the outer articular surface 50 of the femoral component 12 and coating 58.

In some embodiments, the outer sublayer 90 comprises at least about 90% zirconium nitride. In some embodiments, the outer sublayer 90 comprises at least about 95% zirconium nitride.

In some illustrative embodiments, the outer layer 72 is configured to form the outer articular surface 50 of the coating 58 and hence the femoral component 12. The outer layer 72 comprises an inner surface 82 and an outer surface 84. The inner surface 82 of the outer layer 72 is located between the intermediate layer 70 and the outer surface 84 of the outer layer 72. The outer surface 84 of the outer layer 72 forms an outer surface 84 of the femoral component 12. Illustratively, the outer surface 84 of the outer layer 72 forms the outer articular surface 50 of the femoral component 12 and is configured to interact and rotate about the tibial bearing 14, as shown in FIG. 2.

In some examples, the outer layer 72 can be formed by depositing the outer layer 72 or by thermal growth through oxidation of a portion of the intermediate layer 70. In some embodiments, the outer layer 72 has a thickness of at least about 0.2 μm, at least about 0.5 μm, at least about 1 μm, at least about 2 μm, at least about 3 μm, at least about 4 μm, at least about 5 μm, or at least about 6 μm. In some embodiments, the outer layer 72 has a thickness of at least about 50 nm, at least about 100 nm, at least about 150 nm, at least about 200 nm, or at least about 250 nm. When the outer layer 72 is deposited, the outer layer 72 can have a thickness of about 0.5 μm to about 5 μm. When the outer layer 72 is formed by oxidation, the outer layer 72 can have a thickness of about 100 nm to about 200 nm. In some embodiments, the outer layer 72 has a thickness of about 1000 nm, about 1500 nm, about 1800 nm, about 1900 nm, about 2000 nm, about 2400 nm, about 2500 nm, about 2800 nm, about 3000 nm, about 3100 nm, or about 3500 nm.

In an illustrative embodiment, the outer layer 72 is formed by oxidizing at least part of the intermediate layer 70. For example, the outer surface 80 of the intermediate layer 70 can be oxidized to thermally grow the outer layer 72. Illustratively, the thermal growing may occur by oxygen inserting into the lattice of portions, for example an outer portion, of the intermediate layer 70 to form an oxide. In some embodiments, the outer layer 72 comprises a ceramic. In illustrative embodiments, the ceramic of the outer layer 72 is an oxide of the composition of the intermediate layer 70. In some embodiments, the outer layer 72 comprises an oxide of a niobium and zirconium alloy. In some embodiments, the outer layer 72 comprises zirconium oxide. In some embodiments, the outer layer 72 comprises niobium oxide. In some embodiments, the outer layer 72 comprises zirconium oxide and niobium oxide. In some embodiments, the outer layer 72 comprises monoclinic zirconium oxide. In some embodiments, the outer layer 72 comprises at least about 90% zirconium oxide. In some embodiments, the outer layer 72 comprises at least about 90% monoclinic zirconium oxide. In some embodiments, the outer layer 72 comprises monoclinic and/or tetragonal zirconium oxynitride. In some embodiments, the outer layer 72 comprises at least about 5% zirconium oxynitride. In some embodiments, the outer layer 72 comprises at least about 2% tetragonal zirconium oxide. In some embodiments, the outer layer 72 comprises at least about 2% cubic zirconium oxide. In some embodiments, the outer layer 72 comprises a ceramic that includes titanium. In one illustrative aspect, the outer layer 72 comprises titanium zirconium nitride. In some embodiments, the outer layer 72 comprises an oxidized metal and titanium.

In illustrative embodiments, the outer layer 72 is formed by depositing the outer layer 72. In some illustrative embodiments, the outer layer 72 comprises deposited zirconium oxide. The deposited zirconium oxide of the outer layer 72 can be tetragonal zirconium oxide or monoclinic zirconium oxide. In an illustrative embodiment, when monoclinic zirconium oxide is deposited, a layer of tetragonal zirconium oxide will form between the monoclinic zirconium oxide and the intermediate layer 70. In some illustrative embodiments, the outer layer 72 is formed by increasing the concentration of oxygen while depositing the outermost sublayer of the intermediate layer 70 such that the outer layer 72 is an oxide of the outermost sublayer of the intermediate layer 70. For example, if the outermost sublayer (e.g., outer sublayer 90) of the intermediate layer 70 is zirconium nitride, the outer layer 72 can be formed by increasing the oxygen concentration of the deposition to form oxidized zirconium nitride, sometimes called zirconium oxynitride. In some embodiments, the outer layer 72 may comprise zirconium oxynitride and niobium oxynitride.

In some embodiments, the third layer may be titanium zirconium nitride. Additionally, in some embodiments, the atomic percent of zirconium in the third layer may be 50 At % to 80 At %. In some embodiments, the atomic percent of zirconium in the third layer may be about 50 At %, about 55 At %, about 60 At %, about 65 At %, about 70 At %, about 75 At %, or about 80 At %. In some embodiments, the atomic percent of zirconium in the third layer may be 30 At % to 85 At %. In some embodiments, the atomic percent of zirconium in the third layer may be about 30 At %, about 35 At %, about 40 At %, about 45 At %, about 50 At %, about 55 At %, about 60 At %, about 65 At %, about 70 At %, about 75 At %, about 80 At %, or about 85 At %.

In some embodiments, the bonding layer 68 comprises zirconium, the intermediate layer 70 comprises at least one zirconium nitride sublayer 86 and at least one niobium nitride sublayer 88, and the outer layer 72 comprises oxidized zirconium.

Figure 4:
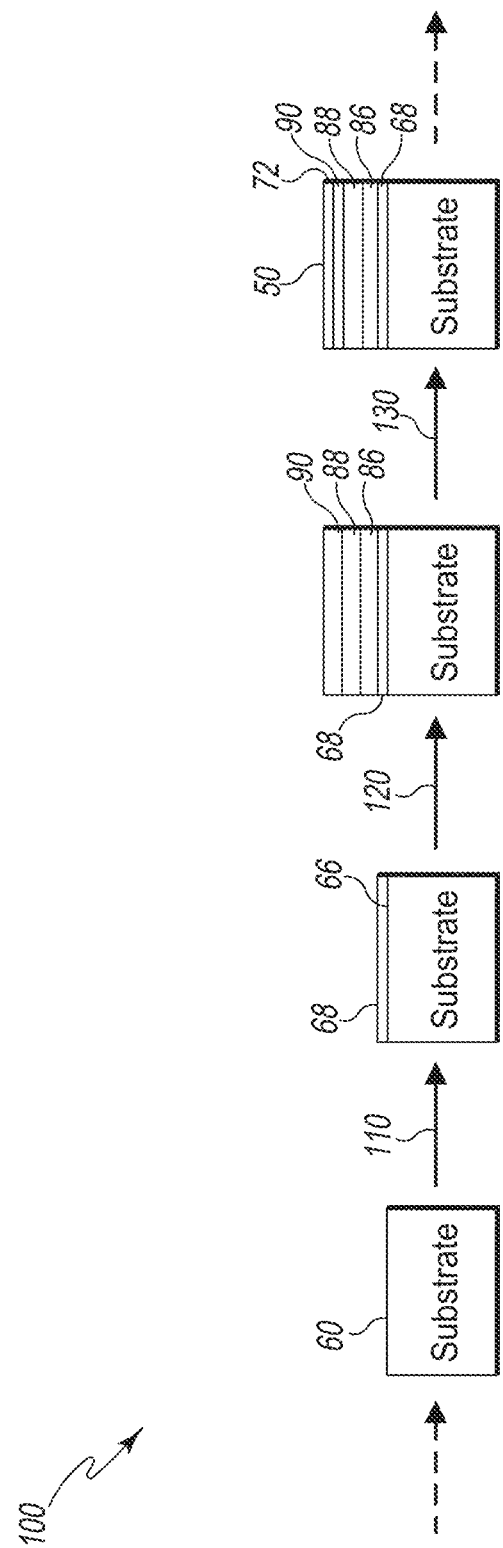
FIG. 4 is an illustrative diagrammatic view of a process for forming the coating of the femoral component of FIGS. 1-3.

Referring now to FIG. 4, the femoral component 12 of an orthopaedic knee prosthesis 10 may be formed through a process 100. In some embodiments, the process 100 comprises a first depositing step 110 of depositing the bonding layer 68, a second depositing step 120 of depositing the intermediate layer 70, and an oxidizing step 130. In illustrative embodiments, the process 100 includes the steps of preparing the substrate 60 for the step of depositing 110. In some embodiments, the process 100 includes finishing steps after the step of oxidizing 130 such as polishing.

Referring now to FIGS. 6-9, shown are illustrative diagrammatic embodiments of a femoral component 12. Illustratively, A denotes a sublayer and is shown in optionally repeating stack with a sublayer of zirconium nitride as shown in FIGS. 6-9.

Referring now to FIGS. 10-15, shown are illustrative diagrammatic embodiments of a femoral component 12. In each example, A denotes a portion of the substrate 60, B denotes a layer or sublayer comprising niobium, C denotes a layer or sublayer comprising zirconium nitride, one B and one C together form a bilayer, and D denotes a layer comprising niobium nitride. In some embodiments, the outer layer 72 of C denotes a layer comprising Ti-doped zirconium nitride. As shown illustratively in FIGS. 10-15, the bonding layer 68 comprises niobium. In some embodiments, bonding layer 68 may comprise niobium, zirconium, titanium, tantalum, platinum, molybdenum, alloys thereof, or combinations thereof.

As shown in the embodiment of FIG. 10, the intermediate layer 70 includes a number of alternating sublayers (C and B) such that n=24 and the outer layer 72 is a single layer C. In the embodiment of FIG. 11, the intermediate layer 70 is a single layer D. In this embodiment, single layer D may be further processed to form the outer articular surface 50 (e.g., oxidized). In the embodiment of FIG. 12, the intermediate layer 70 includes a number of alternating sublayers (C and B) and (C and D) such that n=24 and the outer layer 72 is a single layer C. In the embodiment of FIG. 13, the intermediate layer 70 includes a number of alternating sublayers (C and D) and (B and C) such that n=24 and the outer layer 72 is a single layer C. In the embodiment of FIG. 14, the intermediate layer 70 includes a number of alternating sublayers (C-D-C-B) such that n=24 and the outer layer 72 is a single layer C. In the embodiment of FIG. 15, the intermediate layer 70 includes a number of alternating sublayers (C and D) such that n=24 and the outer layer 72 is a single layer C.

The intermediate layer 70 can be a single layer, such as the layer comprising niobium nitride in FIG. 11. Alternatively, the intermediate layer 70 can include repeating stacks of layers. In some embodiments, the intermediate layer 70 comprises a repeating stack of a sublayer comprising zirconium nitride and a sublayer comprising niobium, as illustratively shown in FIG. 10. In some embodiments, the intermediate layer 70 comprises a first repeating stack of a sublayer 86 comprising zirconium nitride and a sublayer 88 comprising niobium and a second repeating stack of a sublayer 86 comprising zirconium nitride and a sublayer 88 comprising niobium nitride, as illustratively shown in FIGS. 12 and 13. In some embodiments, the intermediate layer 70 comprises a repeating stack of a sublayer 86 comprising zirconium nitride, a sublayer 88 comprising niobium nitride, a sublayer 86 comprising zirconium nitride, and a sublayer 90 comprising niobium, as illustratively shown in FIG. 14. In some embodiments, the intermediate layer 70 comprises a repeating stack of a sublayer 86 comprising zirconium nitride and a sublayer 88 comprising niobium nitride, as illustratively shown in FIG. 15.

In the illustrative embodiments of FIGS. 10-15, the bonding layer 68 has a thickness of about 0.5 μm or about 5 μm. Each sublayer 86 and 88, except for the sublayer 90 furthest the substrate, of the intermediate layer 70 has a thickness of about 125 nm. Illustratively, each of the embodiments in FIGS. 10-15 includes an outer sublayer 90 of zirconium nitride having a thickness of about 3 μm. This outer layer can optionally undergo further processing to form the outer layer 72.

Figure 17:
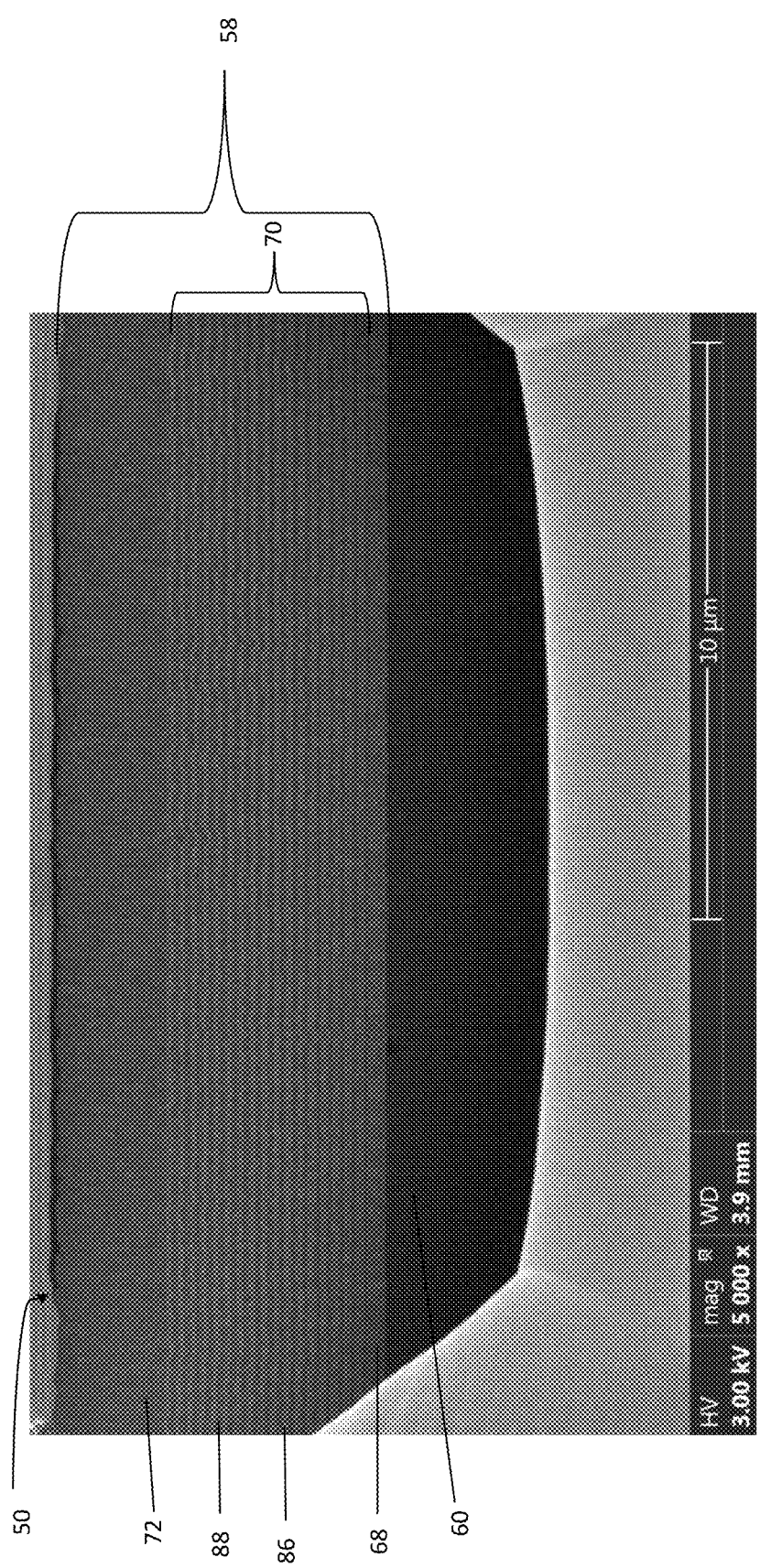
FIG. 17 is an SEM image of a FIB cross-section of MLG-nom.

Alternatively, the intermediate layer 70 may comprise repeating sublayer sequences, wherein repeats have a uniform thickness throughout the span of the intermediate layer 70 but the individual sublayers' thicknesses vary. Referring to FIG. 17, sublayers 86 and 88 are stacked in a repeating sequence with each repeat having a combined thickness that is uniform in the intermediate layer 70, but each individual thickness of sublayer 86 or sublayer 88 is varied. For example, the percentage thickness of sublayer 86 may decrease incrementally and the percentage thickness of sublayer 88 may increase incrementally for each subsequent sequence. In one embodiment, a sublayer 86 may be 75% of the combined thickness and sublayer 88 may be 25% of the combined thickness of the first sequence. Then in the second sequence, sublayer 86 may comprise 70% and sublayer 88 may comprise 30%. Following that, the third sequence may comprise 65% sublayer 86 and 35% sublayer 88. In this manner, sublayer 86 and sublayer 88 are graded stepwise over the span of the intermediate layer 70. In some embodiments, sublayer 86's presence in a sequence is reduced by 5% in each subsequent sequences and sublayer 88's presence in a sequence is increased by 5% over the span of intermediate layer 70. Accordingly, each sequence of sublayer 86 and sublayer 88 maintains a uniform thickness throughout the span of intermediate layer 70. Further exemplary embodiments are provided in Tables 3, 4, and 5. In some embodiments, the amount present of sublayer 86 in a sequence reduces by about 2%, about 3%, about 4%, about 5%, about 6% about 7%, about 8%, about 9% about 10%, about 11%, about 12%, about 13%, about 14%, about 15%, about 16%, about 17%, about 18%, about 19%, about 20%, about 21%, about 22%, about 23%, about 24%, or about 25% in each subsequent sequence. Reciprocally, in some embodiments, the amount present of sublayer 88 increases about 2%, about 3%, about 4%, about 5%, about 6% about 7%, about 8%, about 9% about 10%, about 11%, about 12%, about 13%, about 14%, about 15%, about 16%, about 17%, about 18%, about 19%, about 20%, about 21%, about 22%, about 23%, about 24%, or about 25% in each subsequent sequence.

In some embodiments, the first depositing step 110 deposits a material and forms the bonding layer 68 on the condylar surface 66 of the substrate 60. In some embodiments, the first depositing step 110 is performed by physical vapor deposition (PVD). In some embodiments, the first depositing step 110 is performed by a magnetron sputter system. In other embodiments, PVD may be performed using HiPIMS, IBAD, or other deposition systems.

In some embodiments, the second depositing step 120 forms the intermediate layer 70 on the outer surface 76 of the bonding layer 68. In some embodiments, the second depositing step 120 is performed by PVD. In some embodiments, the step of depositing 120 is performed by a magnetron sputter system.

In some embodiments, the second depositing step 120 comprises depositing the inner sublayer 86. Illustratively, the inner sublayer 86 is deposited onto the bonding layer 68 by the second depositing step 120.

In some embodiments, the second depositing step 120 comprises depositing the intermediate sublayer 88 onto the inner sublayer 86. In illustrative embodiments, the second step of depositing 120 includes repeating the steps of depositing the inner sublayer 86 and the intermediate sublayer 88 until a desired number of sublayers is achieved. Then, the outer sublayer 90 may be deposited on the outermost deposited sublayer (e.g., the inner sublayer 86 or the intermediate sublayer 88).

In some embodiments, the second depositing step 120 comprises depositing the outer sublayer 90 onto the intermediate sublayer 88. In illustrative embodiments, the second step of depositing 120 includes repeating the steps of depositing the inner sublayer 86, the intermediate sublayer 88, and the outer sublayer 90 until a desired number of sublayers is achieved. Optionally, a final outer sublayer 90 is deposited on the outermost sublayer (e.g., the inner sublayer 86, the intermediate sublayer 88, or the outer sublayer 90).

In some embodiments, the second depositing step 120 comprises depositing a zirconium nitride inner sublayer 86 onto the bonding layer 68, depositing a niobium nitride intermediate sublayer 88 on the zirconium nitride inner sublayer 86, and depositing a zirconium nitride outer sublayer 90 on the niobium nitride intermediate sublayer 88.

In some embodiments, the second depositing step 120 is performed to produce a number of alternating sublayers of the zirconium nitride inner sublayer 86 and the niobium nitride intermediate sublayer 88. In some embodiments, the steps of depositing the zirconium nitride inner sublayer 86 and the niobium nitride intermediate sublayer 88 are repeated until a desirable thickness is obtained. In some embodiments, the thickness is up to 6 μm.

In some embodiments, the second depositing step 120 deposits an outer sublayer 90 of zirconium nitride for subsequent processing.

In some embodiments, the step of depositing 120 is performed by PVD. In some embodiments, the first depositing step 110 is performed by a magnetron sputter system. In other embodiments, PVD may be performed using HiPIMS, IBAD, or other deposition systems.

In some embodiments, the oxidizing step 130 oxidizes a portion of the intermediate layer 70 to form the outer layer 72. In some embodiments, the oxidizing step 130 is performed as described in U.S. Pat. Nos. 6,447,550 and 5,324,009, the entirety of each of which is expressly incorporated herein by reference. In some embodiments, the oxidizing step 130 oxidizes at least a portion of the outer surface 80 of the intermediate layer 70. In some embodiments, the oxidizing step 130 oxidizes at least a portion of the zirconium nitride outer sublayer 90 into oxidized zirconium thus forming the outer layer 72. In some embodiments, the oxidizing step 130 oxidizes, partially or completely, the exposed surface of the zirconium nitride outer sublayer 90 into monoclinic oxidized zirconium. In some embodiments, the outer layer 72 comprises zirconium oxynitride. In some embodiments, the outer layer 72 comprises at least about 5% zirconium oxynitride.

In some embodiments, the oxidizing step 130 is performed by heating an environment comprising oxygen. In some embodiments, the environment is at a temperature of least 500° C. or about 540° C. In some embodiments, the environment is at a temperature of about 500° C. to about 600° C. In an illustrative embodiment, the environment comprises about 2.5% oxygen in argon. In some embodiments, the oxidizing step 130 is performed for about 5 hours.

In alternative embodiments, the process 100 comprises a step of depositing the outer layer 72 (not shown). The step of depositing the outer layer 72 is performed by PVD, which may be performed using a magnetron sputter system. In other embodiments, PVD may be performed using HiPIMS, IBAD, or other deposition systems. In some embodiments, the step of depositing the outer layer 72 deposits a layer of ceramic, for example zirconium oxide.

In some embodiments, the deposited zirconium oxide forming the outer layer 72 comprises tetragonal, monoclinic, or cubic zirconium oxide. In some embodiments, the deposited zirconium oxide forming the outer layer 72 comprises tetragonal, monoclinic, or cubic zirconium oxynitride.

Figure 19:
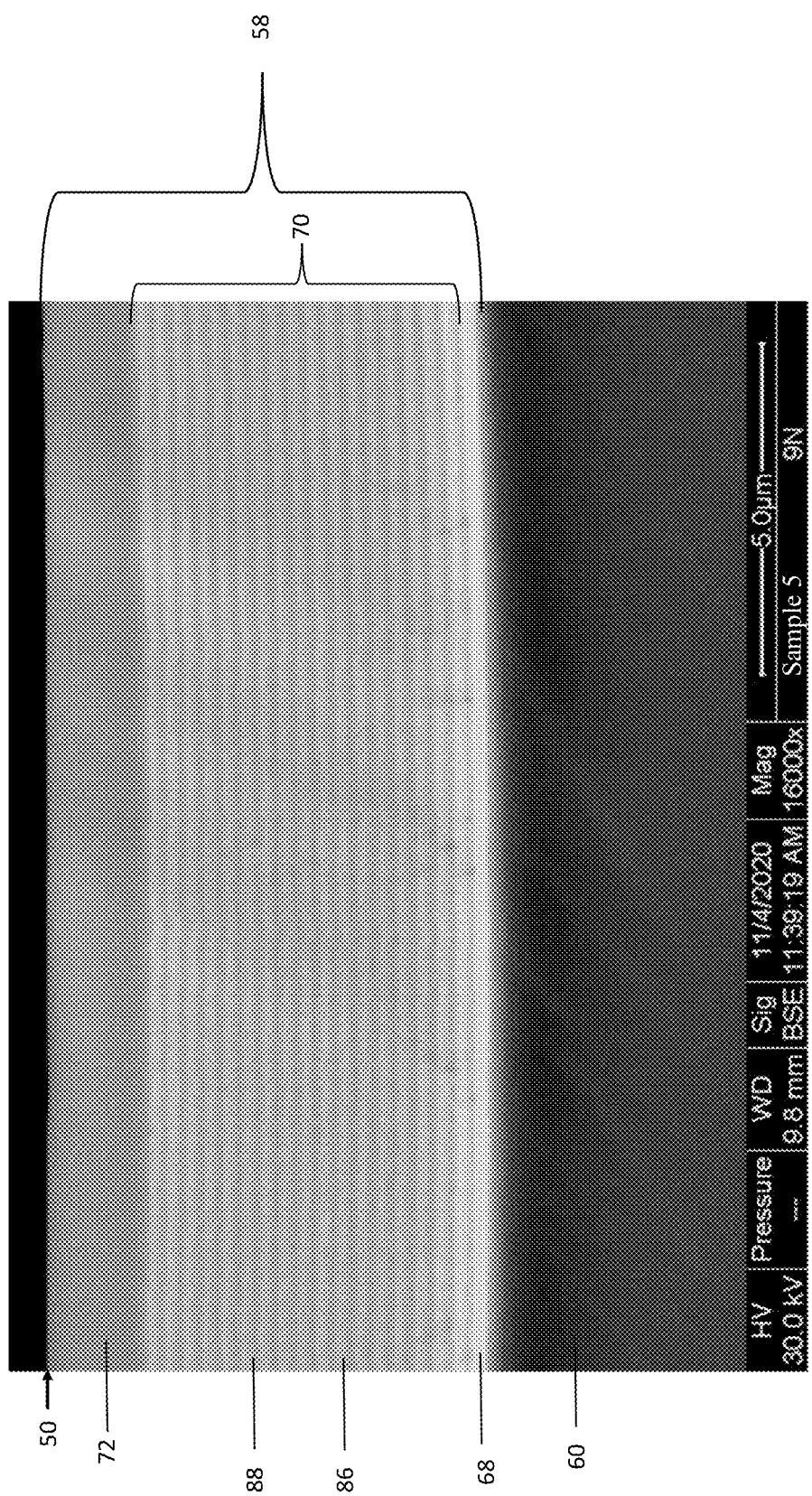
FIG. 19 is an SEM image of a FIB cross-section of ML-Nom.
Figure 20:
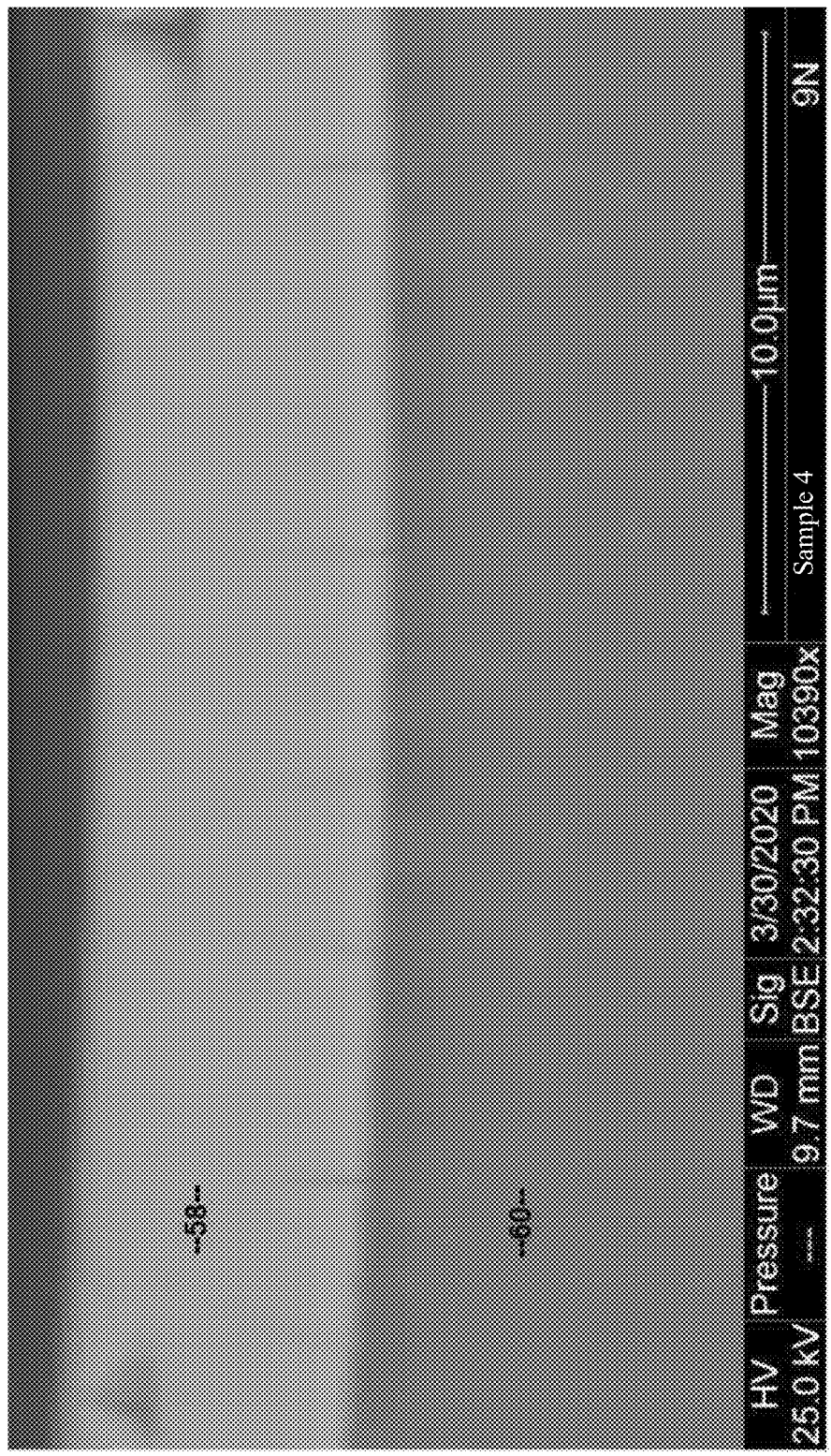
FIG. 20 is an SEM image of a FIB cross-section of Mono-10.

In some embodiments, the coating 58 is configured to resist chipping when a force is applied. For example, the embodiment of FIG. 19, shows the ability of a multi-layer coating 58 to resist chipping and arrest cracking when a force of about 9 N is applied. Cracking occurs when the tensile strength of the material fails and begins to fracture. As is illustrated in FIG. 19, the niobium sublayer arrests the cracks that are forming in the zirconium nitride sublayers. Compare the toughness and ductility to FIG. 20. As illustrated in FIG. 20, a monolayer of zirconium nitride developed much longer cracks compared to the multilayer coating (i.e., Sample 5 discussed below) in FIG. 19.

EXAMPLES

In the following Examples, a series of monolayer zirconium nitride (ZrN) coatings with a niobium (Nb) bonding layer were produced and tested. Additionally, various multilayer Nb/ZrN coatings of varying architecture and thickness were produced and tested. Table 1 provides information on each sample. Sample coatings 1-11 used a Nb bonding layer of about 140 nm to 400 nm to facilitate adhesion between the Ti-6Al-4V substrate and the coating. The coatings were prepared by deposition using either magnetron sputtering with enrichment of the plasma with ions produced by thermionic emission (Sample 5) from electrodes using the chamber walls as the anode (Plasma Enhanced Magnetron Sputtering), or via unbalanced magnetron sputtering to achieve the same objective of increasing the ionization rate of the plasma. The unbalanced magnetron deposition was performed on a Flexicoat 1200 platform. Deposition parameters were selected from a series of experimental runs performed prior to producing the test samples described below.

TABLE 1

Sample Descriptions

| Sample No. | Coating Name | Coating Type Monolayer (M) Multilayer (ML) | Material of Each Layer | Total Coating Thickness |
|---|---|---|---|---|
| 1 | Mono-2 | M | Nb—ZrN | 2 microns |
| 2 | Mono-5 | M | Nb—ZrN | 5 microns |
| 3 | Mono-8 | M | Nb—ZrN | 8 microns |
| 4 | Mono-10 | M | Nb—ZrN | 10 microns |
| 5 | ML-nom | ML | Nb—[Nb/ZrN]$_{17}$—ZrN | 9 microns |
| 6 | ML+20 | ML | Nb—[Nb/ZrN]$_{17}$—ZrN | 10.7 microns |
| 7 | ML-20 | ML | Nb—[Nb/ZrN]$_{17}$—ZrN | 7 microns |
| 8 | ML-40 | ML | Nb—[Nb/ZrN]$_{17}$—ZrN | 5.2 microns |
| 9 | MLG-nom | ML | Nb—[Nb/ZrN]$_{17}$—ZrN | 7 microns |
| 10 | MLG+25 | ML | Nb—[Nb/ZrN]$_{17}$—ZrN | 8.7 microns |
| 11 | MLG-25 | ML | Nb—[Nb/ZrN]$_{17}$—ZrN | 5.5 microns |

Commerical Comparator

| Sample No. | Name | Monolayer (M) | Material | Coating Thickness |
|---|---|---|---|---|
| 12 | LCS TiN | M | TiN | 10 microns |

Monolayer (Samples 1-4): Ti-Al6-V4 ("Ti-6-4") coupons were polished to less than 40 nm roughness average (Ra) and were cleaned in preparation for thin film deposition. Four monolayer ZrN coatings with thicknesses ranging from 2 μms to 10 μms were produced by unbalanced magnetron sputtering in a Flexicoat 1200 coating platform. Coating thickness was verified by examination of cross sections produced by either mounting and cross sectioning or by Focused Ion Beam (FIB) followed by examination in a scanning electron microscope (SEM).

Figure 16:
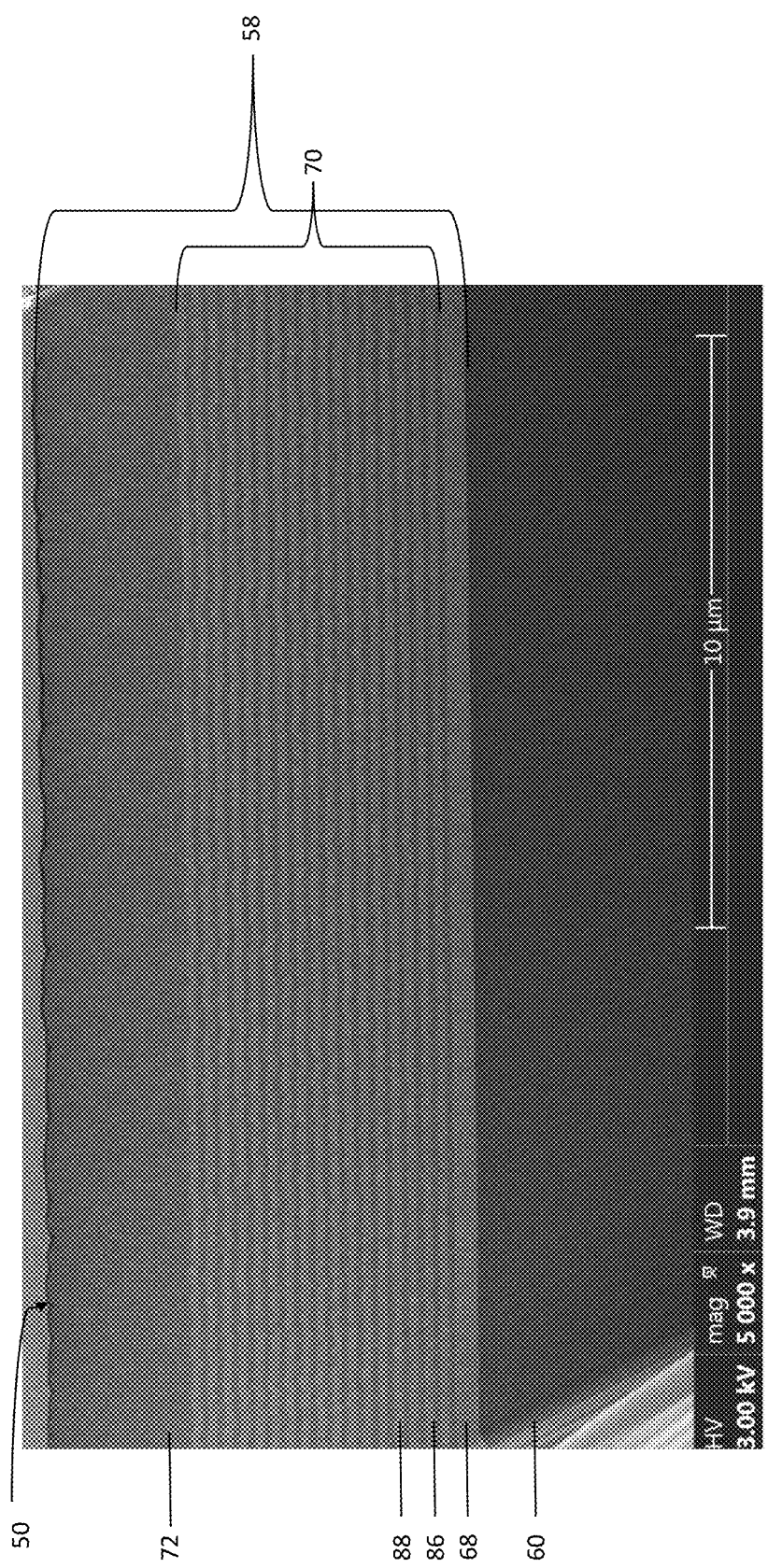
FIG. 16 is an SEM image of a FIB cross-section of ML-nom.

Multilayer (Samples 5-8): Ti-6-4 coupons were polished to less than 40 nm Ra and were cleaned in preparation for thin film deposition. A series of multilayer Nb/ZrN coatings were produced by unbalanced magnetron sputtering in a Flexicoat 1200 coating platform. Thickness of the various sublayers within the intermediate layer were determined by examination of cross sections produced by either mounting and cross sectioning or by FIB sectioning followed by examination in an SEM. All multilayered coatings (i.e., Samples 5-11) had 34 sublayers, or described below as 17 bilayers, of Nb/ZrN with Nb representing 55-60% of the bilayer thickness. Sample 5, designated ML-nom is a coating designed as having a potential nominal thickness with each Nb/ZrN bilayer having a thickness of about 300 nm, a ZrN outer layer thickness of about 2500 nm, and a Nb bonding layer thickness of about 400 nm. This coating is shown in cross-section in FIG. 16 with the layer thicknesses summarized in Table 2. Three additional multilayer (ML) coatings were produced by growing all layers by 20% (ML+20), shrinking all layers by 20% (ML-20), and shrinking all layers by 40% (ML-40) as compared to ML-nom (Sample 5). Samples 5-8 are summarized in Table 2.

TABLE 2

Thicknesses and parameters of the Multilayer Coatings (Samples 5 through 8)

| Sample No. | ZrN Outer Layer (nm) | # of bi-layers | Bi-Layer Composition | | Nb bonding layer (nm) | Total Coating thickness (nm) |
|---|---|---|---|---|---|---|
| | | | ZrN sublayer (nm) | Nb sublayer (nm) | | |
| 5 | 2500 | 17 | 136 | 178 | 400 | 8238 |
| 6 | 3100 | 17 | 163.2 | 213.6 | 480 | 9985.6 |
| 7 | 1900 | 17 | 108.8 | 142.4 | 320 | 6490.4 |
| 8 | 1500 | 17 | 81.6 | 106.8 | 240 | 4702.8 |

Multilayer Graded (Samples 9-11): Finally, coatings with a graded stiffness were prepared in a series of 3 multilayer graded coatings with the same bilayer number (i.e., 17) of the non-graded structures described above, but with the % Nb in the first bilayer set to about 75% of the bilayer thickness and then reduced by 5% in subsequent bilayer's such that bilayer 17 contained about 33% Nb. A potential nominal graded coating with 2400 nm ZrN outer layer and total thickness of 8738 nm was produced and is identified as MLG-Nom (i.e., Sample 9) and is shown in FIB cross section in FIG. 17 and summarized in Table 3. All layers were increased by 25% (MLG+25) and reduced by 25% in MLG-25 with summary thicknesses shown in Tables 4 and 5.

TABLE 3

Thicknesses and parameters of the Multilayer Graded Coating MLG-Nom (Sample 9)
Thickness of Coating Components

| Bilayer # within the intermediate layer | Nb sublayer (nm) | ZrN sublayer (nm) | Bilayer thickness |
|---|---|---|---|
| 1 | 188 | 63 | 251 |
| 2 | 179 | 73 | 251 |
| 3 | 170 | 82 | 251 |
| 4 | 161 | 90 | 251 |
| 5 | 153 | 98 | 251 |
| 6 | 145 | 106 | 251 |
| 7 | 138 | 113 | 251 |
| 8 | 131 | 120 | 251 |
| 9 | 125 | 126 | 251 |
| 10 | 118 | 133 | 251 |
| 11 | 113 | 139 | 251 |
| 12 | 107 | 144 | 251 |
| 13 | 102 | 150 | 251 |
| 14 | 97 | 155 | 251 |
| 15 | 92 | 160 | 251 |
| 16 | 87 | 164 | 251 |
| 17 | 83 | 168 | 251 |
| Nb bonding layer (nm) | | | 320 |
| ZrN outer layer (nm) | | | 2400 |
| Total Coating thickness (nm) | | | 6990 |

TABLE 4

Thickness and parameters of the Multilayer Graded Coating MLG+25 (Sample 10)
Thickness of Coating Components

| Bilayerlayer # within the intermediate layer | Nb sublayer (nm) | ZrN sublayer (nm) | Bilayer thickness (nm) |
|---|---|---|---|
| 1 | 235 | 79 | 314 |
| 2 | 223 | 91 | 314 |
| 3 | 212 | 102 | 314 |
| 4 | 201 | 113 | 314 |
| 5 | 191 | 123 | 314 |
| 6 | 182 | 132 | 314 |
| 7 | 173 | 141 | 314 |
| 8 | 164 | 150 | 314 |
| 9 | 156 | 158 | 314 |
| 10 | 148 | 166 | 314 |
| 11 | 141 | 173 | 314 |
| 12 | 134 | 180 | 314 |
| 13 | 127 | 187 | 314 |
| 14 | 121 | 193 | 314 |
| 15 | 115 | 199 | 314 |
| 16 | 109 | 205 | 314 |
| 17 | 103 | 211 | 314 |
| Nb bonding layer (nm) | | | 400 |
| ZrN outer layer (nm) | | | 3000 |
| Total Coating thickness (nm) | | | 8738 |

TABLE 5

Thickness and parameters of the Multilayer Graded Coating MLG-25 (Sample 11)
Thickness of Coating Components

| Bilayer # within the intermediate layer | Nb sublayer (nm) | ZrN sublayer (nm) | Bilayer thickness nm) |
|---|---|---|---|
| 1 | 141 | 47 | 188 |
| 2 | 134 | 54 | 188 |
| 3 | 127 | 61 | 188 |
| 4 | 121 | 68 | 188 |

TABLE 5-continued

Thickness and parameters of the Multilayer Graded Coating MLG-25 (Sample 11)
Thickness of Coating Components

| Bilayer # within the intermediate layer | Nb sublayer (nm) | ZrN sublayer (nm) | Bilayer thickness nm) |
|---|---|---|---|
| 5 | 115 | 74 | 188 |
| 6 | 109 | 79 | 188 |
| 7 | 104 | 85 | 188 |
| 8 | 98 | 90 | 188 |
| 9 | 94 | 95 | 188 |
| 10 | 89 | 100 | 188 |
| 11 | 84 | 104 | 188 |
| 12 | 80 | 108 | 188 |
| 13 | 76 | 112 | 188 |
| 14 | 72 | 116 | 188 |
| 15 | 69 | 120 | 188 |
| 16 | 65 | 123 | 188 |
| 17 | 62 | 126 | 188 |
| Nb bonding layer (nm) | | | 240 |
| ZrN outer layer (nm) | | | 1800 |
| Total coating thickness (nm) | | | 5243 |

Control (Sample 12): Samples 5-11 were compared to the monolayered coatings (Samples 1-4) and a commercially available coating to demonstrate the advantages and improvements in the described coatings.

Scratch testing. A scratch test was developed that reproduced scratches observed on Cobalt chromium (CoCr) femoral retrievals. A diamond tip with either a 20 μm or 200 μm radius, applied loads from 1-6 Newtons (N) or from 3-36 N, respectively, to reproduce the majority of scratches on retrievals and was applied to the Monolayer and Multilayer samples described above as well as the Commercial Comparator.

Figure 18:
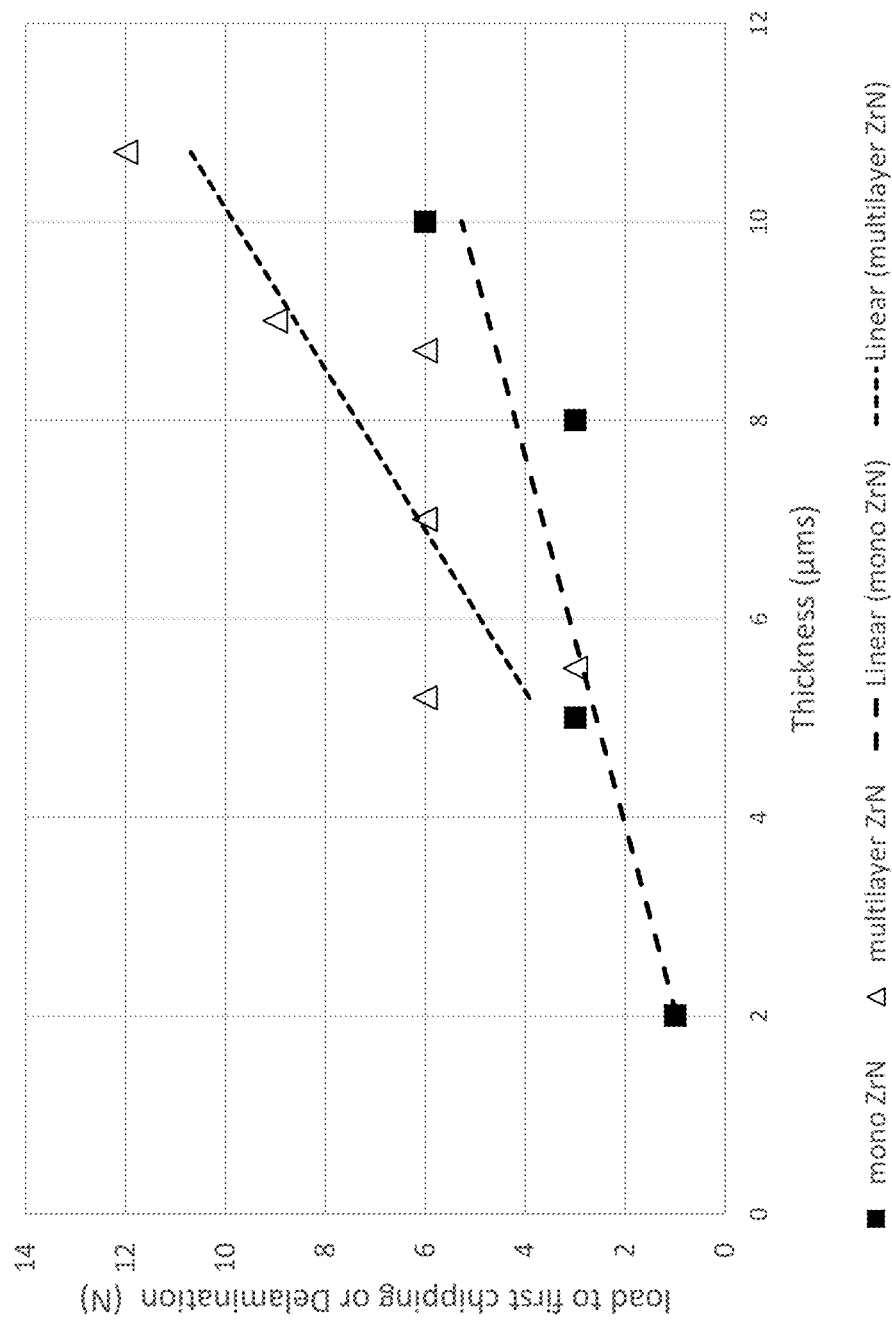
FIG. 18 is a graph showing the minimum load applied by a 20 micron tip to first chipping or delamination observed in the various coating samples.
Figure 21:
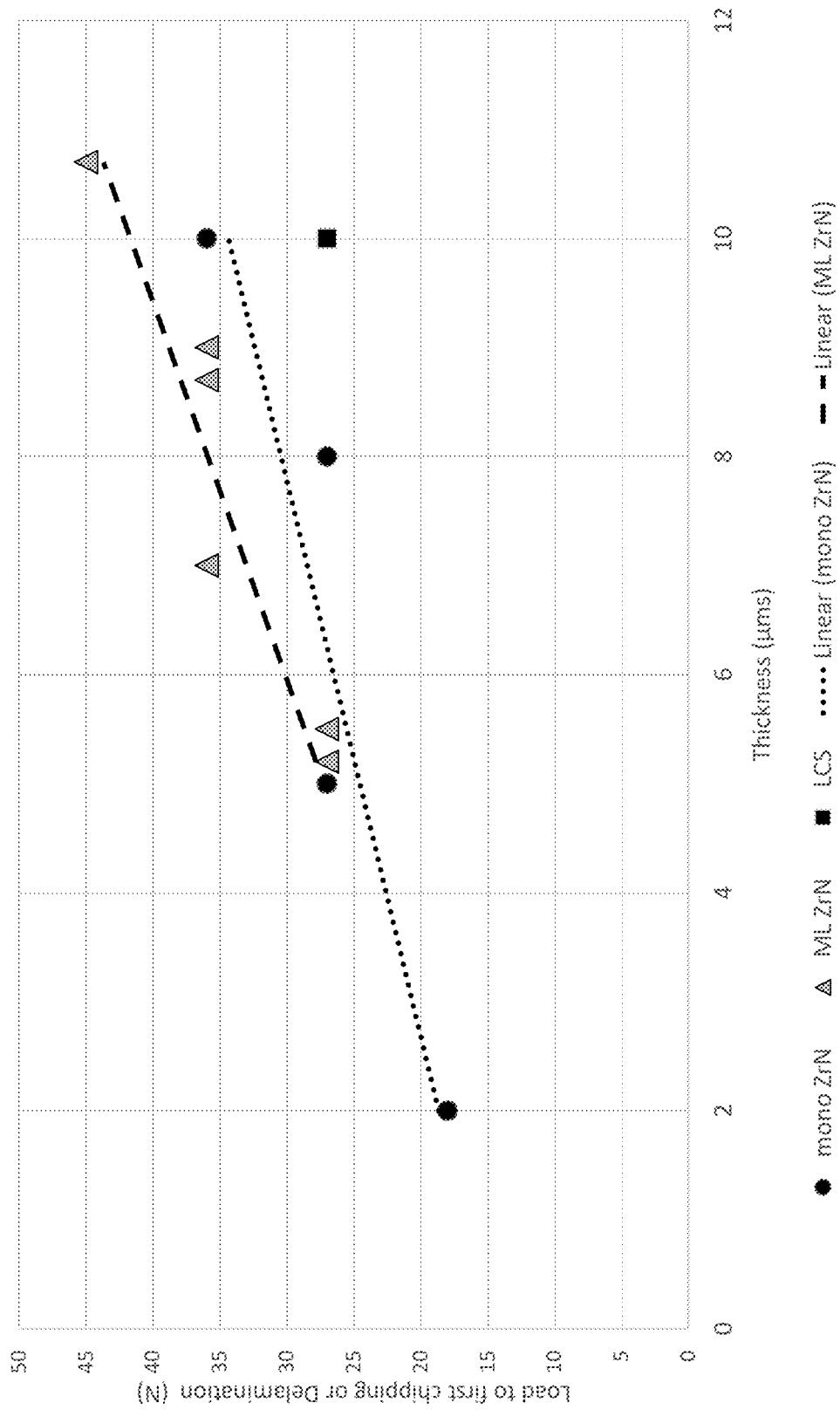
FIG. 21 is a graph showing the minimum load applied by a 200 micron tip to first chipping or delamination observed in various coating samples.

The results shown in FIG. 18 and FIG. 21 and tabulated in Table 6 and Table 7, respectively, show that the multilayer Nb/ZrN samples resisted chipping and delamination better than those produced with a monolayer of ZrN (Samples 2 and 4) and to a similar extent as the Commercial Comparator (Sample 12) of similar thickness. FIG. 19 shows a cross section of multilayer coating ML-Nom (Sample 5) after scratch testing, which shows how the ductile Nb layers arrest cracks that begin in the harder and more brittle ZrN layers.

TABLE 6

Results of Scratch Test (shown graphically in FIG. 18) on the various coating samples with increasing force.

| Sample Name | 20 μm Indenter | | | |
|---|---|---|---|---|
| (No.) | 1N | 3N | 6N | 9N |
| Mono-2 (1) | Chipping | Delam | Delam | Delam |
| Mono-5 (2) | | Chipping | Delam | Delam |
| Mono-8 (3) | | Chipping | Chipping | Chipping |
| Mono-10 (4) | | | Chipping | Chipping |
| ML-nom (5) | | | | Chipping |
| ML+20 (6) | | | | |
| ML-20 (7) | | | Chipping | Delam |
| ML-40 (8) | | | Delam | Delam |
| MLG-nom (9) | | | Chipping | Delam |
| MLG+25 (10) | | | Chipping | Chipping |
| MLG-25 (11) | | Chipping | Chipping | Chipping |

TABLE 7

Results of Scratch Test (shown graphically in FIG. 21) on the various samples with increasing force.

| Sample Name | 200 μm Indenter | | | | | |
|---|---|---|---|---|---|---|
| (No.) | 3N | 6N | 9N | 18N | 27N | 36N |
| Mono-2 (1) | | | | Chipping | Delam | Delam |
| Mono-5 (2) | | | | | Chipping | Delam |
| Mono-8 (3) | | | | | Chipping | Chipping |
| Mono-10 (4) | | | | | | Chipping |
| ML-nom (5) | | | | | | Chipping |
| ML+20 (6) | | | | | | |
| ML-20 (7) | | | | | | Delam |
| ML-40 (8) | | | | | Chipping | Delam |
| MLG-nom (9) | | | | | | Chipping |
| MLG+25 (10) | | | | | | Chipping |
| MLG-25 (11) | | | | | Chipping | Delam |
| LCS TiN (12) | | | | | Chipping | Delam |

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic knee implant comprising:
a femoral component configured to be coupled to a distal end of a patient's femur, the femoral component comprising
(i) a substrate comprising a titanium alloy having (a) a condylar surface that is curved in a sagittal plane and (b) a bone-facing surface positioned opposite the condylar surface; and
(ii) a coating disposed on the condylar surface, the coating comprising (a) a bonding layer comprising niobium, zirconium, titanium, tantalum, platinum, molybdenum, an alloy thereof, or combinations thereof, (b) an outer ceramic layer, and (c) a second layer comprising a plurality of alternating sublayers positioned between and interconnecting the bonding layer and the outer ceramic layer, wherein at least one sublayer of the second layer has a thickness of about 5 nm to about 500 nm, and wherein at least one sublayer of the second layer comprises at least about 95% niobium nitride,
wherein (i) the plurality of alternating sublayers are configured to resist crack propagation from the outer ceramic layer, the plurality of alternating sublayers include a number of metallic sublayers and a number of ceramic sublayers that are harder than the metallic sublayers, and (ii) the outer ceramic layer forms an outer articular surface of the femoral component and is shaped to contact a concave proximal surface of a tibial bearing.

2. The implant of claim 1, wherein the second layer comprises at least eight sublayers, wherein the sublayers comprise alternating zirconium nitride and niobium nitride sublayers.

3. The implant of claim 2, wherein each zirconium nitride sublayer of the alternating sublayers has a thickness of about 5 nm to about 200 nm.

4. The implant of claim 3, wherein the second layer has a thickness of about 3 µm to about 8 µm.

5. The implant of claim 1, wherein the outer ceramic layer comprises at least about 90% monoclinic oxidized zirconium.

6. The implant of claim 5, wherein the outer ceramic layer has a thickness of about 100 nm to about 5 µm.

7. The implant of claim 6, wherein at least one sublayer of the second layer comprises at least about 95% zirconium nitride.

8. The implant of claim 1, wherein the bonding layer comprises at least about 90% zirconium.

9. The implant of claim 8, wherein the bonding layer has a thickness of about 50 nm to about 2 µm.

10. The implant of claim 1, wherein the femoral component comprises a bone-engaging layer disposed on the bone-facing surface.

11. The implant of claim 10, wherein the bone-engaging layer is porous.

12. The implant of claim 1, wherein the second layer comprises an inner sublayer and an outer sublayer.

13. The implant of claim 12, wherein the inner sublayer and the outer sublayer have the same composition.

14. The implant of claim 12, wherein the second layer comprises an intermediate sublayer having a composition different from the inner sublayer, the outer sublayer, or both.

15. A process for forming a femoral component of an orthopaedic knee implant, the process comprising:
    depositing a first layer comprising niobium, zirconium, titanium, tantalum, platinum, molybdenum, or combinations thereof on a condylar surface of a substrate comprising titanium, wherein the condylar surface is curved in a sagittal plane; and
    depositing one or more alternating sublayers to form a second layer,
    wherein depositing the alternating sublayers to form the second layer comprises:
    (a) creating a sublayer of zirconium nitride on the first layer,
    (b) creating a sublayer of niobium on the sublayer of zirconium nitride, and
    (c) repeating steps (a) and (b) to form the second layer.

16. The process of claim 15, comprising oxidizing a portion of the second layer to form a third layer comprising oxidized zirconium.

17. The process of claim 15, comprising depositing a third layer on an outer surface of the second layer.

18. The process of claim 17, wherein the third layer comprises zirconium oxide, niobium oxide, zirconium oxynitride, niobium oxynitride, or a combination thereof.

19. An orthopaedic knee implant comprising:
    a femoral component configured to be coupled to a distal end of a patient's femur, the femoral component comprising
    (i) a substrate comprising a titanium alloy having (a) a condylar surface that is curved in a sagittal plane and (b) a bone-facing surface positioned opposite the condylar surface; and
    (ii) a coating disposed on the condylar surface, the coating comprising (a) a bonding layer comprising niobium, zirconium, titanium, tantalum, platinum, molybdenum, an alloy thereof, or combinations thereof, (b) an outer ceramic layer, and (c) a second layer comprising a plurality of alternating sublayers positioned between and interconnecting the bonding layer and the outer ceramic layer, wherein the second layer comprises an inner sublayer and an outer sublayer, and wherein the second layer comprises an intermediate sublayer having a composition different from the inner sublayer, the outer sublayer, or both,
    wherein (i) the plurality of alternating sublayers are configured to resist crack propagation from the outer ceramic layer, the plurality of alternating sublayers include a number of metallic sublayers and a number of ceramic sublayers that are harder than the metallic sublayers, and (ii) the outer ceramic layer forms an outer articular surface of the femoral component and is shaped to contact a concave proximal surface of a tibial bearing.

20. The implant of claim 19, wherein the second layer comprises at least eight sublayers of alternating zirconium nitride and niobium nitride sublayers.

21. The implant of claim 19, wherein the outer ceramic layer comprises at least about 90% monoclinic oxidized zirconium.

22. The implant of claim 19, wherein at least one sublayer of the second layer has a thickness of about 5 nm to about 500 nm.

23. The implant of claim 19, wherein the bonding layer comprises at least about 90% zirconium.

* * * * *